US012570028B2

(12) United States Patent
Farris et al.

(10) Patent No.: US 12,570,028 B2
(45) Date of Patent: *Mar. 10, 2026

(54) IMPLANTABLE MEDICAL DEVICE WITH VARIED COMPOSITION AND POROSITY, AND METHOD FOR FORMING SAME

(71) Applicant: HAPPE SPINE LLC, Grand Rapids, MI (US)

(72) Inventors: Jeffery A. Farris, Beme, IN (US); Kevin Lee Brown, Fort Wayne, IN (US); Douglas B. Snell, Overland Park, KS (US); Ryan K. Roeder, Granger, IN (US); Mark G. Messman, Larwill, IN (US)

(73) Assignee: HAPPE SPINE LLC, Grand Rapids, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/656,644

(22) Filed: May 7, 2024

(65) Prior Publication Data

US 2024/0286320 A1 Aug. 29, 2024

Related U.S. Application Data

(63) Continuation of application No. 17/870,911, filed on Jul. 22, 2022, now Pat. No. 12,005,616, which is a (Continued)

(51) Int. Cl.
*A61L 27/48* (2006.01)
*A61F 2/28* (2006.01)
(Continued)

(52) U.S. Cl.
CPC .............. *B29C 43/006* (2013.01); *A61F 2/28* (2013.01); *A61F 2/30942* (2013.01); (Continued)

(58) Field of Classification Search
CPC ....... B29C 43/00; B29C 43/006; B29C 43/14; B29C 43/32; B29C 2043/144; (Continued)

(56) References Cited

U.S. PATENT DOCUMENTS 6,569,489 B1 5/2003 Li
6,736,849 B2 5/2004 Li et al.
(Continued)

FOREIGN PATENT DOCUMENTS

EP 0706446 A1 4/1996
WO 2009009666 A3 1/2009
(Continued)

OTHER PUBLICATIONS

Barkarmo et al. "Nano-hydroxyapatite-coated PEEK implants: a pilot study in rabbit bone", J Biomed Mater Res A, 2013, 101: 465-471.
(Continued)

*Primary Examiner* — Thu Khanh T. Nguyen
(74) *Attorney, Agent, or Firm* — McNees Wallace & Nurick LLC

(57) ABSTRACT

A method for forming a thermoplastic body having regions with varied material composition and/or porosity. Powder blends comprising a thermoplastic polymer, a sacrificial porogen and an inorganic reinforcement or filler are molded to form complementary parts with closely toleranced mating surfaces. The parts are formed discretely, assembled and compression molded to provide a unitary article that is free from discernible boundaries between the assembled parts. Each part in the assembly has differences in composition and/or porosity, and the assembly has accurate physical features throughout the sections of the formed article, without distortion and nonuniformities caused by variable com-
(Continued)

101 – PROVIDE TWO OR MORE POWDER BLENDS, EACH CONTAINING POLYMER POWDER, OR POLYMER POWDER AND ONE OR MORE OF POROGEN PARTICLE POWDER AND INORGANIC PARTICLE (E.G., REINFORCEMENT)

↓

102 – DISPENSE EACH POWDER BLEND INTO A MOLD (SEPARATE OR LAYERED)

↓

103 – COMPACT EACH DISPENSED POWDER BLEND INTO A PREFORM BY COLD PRESSING OR COMPRESSION MOLDING

↓

104 – MACHINE EACH PREFORM INTO COMPLIMENTARY PARTS

↓

105 – ASSEMBLE MACHINED PARTS TO CONTACT COMPLIMENTARY MATING SURFACES TO FORM AN ARTICLE ASSEMBLY

↓

106 – COMPRESSION MOLD ASSEMBLY TO FORM A UNITARY ARTICLE

↓

107 – OPTIONALLY MACHINE ADDITIONAL FEATURES (OVERALL SHAPE, SURFACES, HOLES/APERTURES, TEETH, RIDGES)

↓

108 – LEACH POROGEN FROM UNITARY ARTICLE paction and densification rates in methods that involve compression molding powder blends in a single step.

20 Claims, 6 Drawing Sheets

Related U.S. Application Data continuation of application No. 17/473,385, filed on Sep. 13, 2021, now Pat. No. 11,426,904, and a continuation of application No. PCT/US2021/050074, filed on Sep. 13, 2021.

(60) Provisional application No. 63/077,308, filed on Sep. 11, 2020.

(51) Int. Cl.

| | |
|---|---|
| *A61F 2/30* | (2006.01) |
| *A61L 27/56* | (2006.01) |
| *B29C 43/00* | (2006.01) |
| *B29C 43/14* | (2006.01) |
| *B29K 101/12* | (2006.01) |
| *B29L 31/00* | (2006.01) |

(52) U.S. Cl.
CPC ........ *A61F 2/30965* (2013.01); *B29C 43/003* (2013.01); *A61F 2002/30957* (2013.01); *B29C 2793/009* (2013.01); *B29K 2101/12* (2013.01); *B29L 2031/7532* (2013.01)

(58) Field of Classification Search
CPC ........ B29C 2043/146; B29C 2043/147; B29C 2043/148
See application file for complete search history.

(56) References Cited

U.S. PATENT DOCUMENTS

| | | | |
|---|---|---|---|
| 6,911,249 | B2 | 6/2005 | Wagner et al. |
| 7,537,664 | B2 | 5/2009 | O'Neill et al. |
| 8,383,024 | B2 | 2/2013 | Morrisette et al. |
| 8,496,710 | B2 | 7/2013 | Bagga et al. |
| 8,562,685 | B2 | 10/2013 | Ulrich, Jr. et al. |
| 8,590,157 | B2 | 11/2013 | Kruth et al. |
| 8,728,387 | B2 | 5/2014 | Jones et al. |
| 8,829,096 | B2 | 9/2014 | Jarman-Smith |
| 9,023,419 | B2 | 5/2015 | Mechan et al. |
| 9,085,665 | B1 | 7/2015 | Chang et al. |
| 9,131,995 | B2 | 9/2015 | Mayfield et al. |
| 9,180,010 | B2 | 11/2015 | Dong et al. |
| 9,314,337 | B2 | 4/2016 | Patterson et al. |
| 9,393,092 | B2 | 7/2016 | Balasundaram et al. |
| 9,456,901 | B2 | 10/2016 | Jones et al. |
| 9,700,431 | B2 | 7/2017 | Nebosky et al. |
| 9,931,438 | B2 | 4/2018 | Kasahara et al. |
| 10,113,502 | B2 | 10/2018 | Maki et al. |
| 10,117,966 | B2 | 11/2018 | Hedrick et al. |
| 10,231,813 | B2 | 3/2019 | Chang et al. |
| 10,405,962 | B2 | 9/2019 | Chang et al. |
| 10,413,427 | B2 | 9/2019 | Trieu |
| 2011/0012280 | A1 | 1/2011 | Deslauriers et al. |
| 2013/0171443 | A1 | 7/2013 | Morrissette et al. |
| 2014/0035201 | A1 | 2/2014 | Jarman-Smith et al. |
| 2014/0236299 | A1 | 8/2014 | Roeder et al. |
| 2015/0018956 | A1 | 1/2015 | Steinmann et al. |
| 2015/0190545 | A1 | 7/2015 | Oral et al. |
| 2017/0119532 | A1 | 5/2017 | McMinn |
| 2019/0192303 | A1 | 6/2019 | Gallagher et al. |
| 2021/0221030 | A1 | 7/2021 | Stoeckl et al. |

FOREIGN PATENT DOCUMENTS

| | | | |
|---|---|---|---|
| WO | 2009029507 | A1 | 3/2009 |
| WO | 2010057949 | A3 | 5/2010 |
| WO | 2011004217 | A1 | 1/2011 |
| WO | 2011107803 | A1 | 9/2011 |
| WO | 2016097721 | A1 | 6/2016 |

OTHER PUBLICATIONS

Basgul et al., "Structure-Property Relationships for 3D printed PEEK Intervertebral Lumbar Cages Produced using Fused Filament Fabrication", 2018 Journal of materials research, 33(14), p. 2040.
Choy et al. "3-dimensional printing for anterior cervical surgery: a review", 2018,Journal of Spine Surgery, 4(4), p. 757.
Garcia-Leiner et al. "Additive Manufacturing of Polyaryletherketones", 2019, In PEEK Biomaterials Handbook (pp. 89-103), William Andrew Publishing.
Zheng et al. "Additively-manufactured PEEK/HA porous scaffolds with highly-controllable mechanical properties and excellent bio-compatibility", Materials Science and Engineering, Sep. 2021, vol. 128, 112333.
Li et al. "Surface sulfonation and nitrification enhance the biological activity and osteogenesis of polyetheretherketone by forming an irregular nano-porous monolayer", 2020, Journal of Materials Science: Materials in Medicine, 31(1), pp. 1-12.
Poulsson et al. Osseointegration of machined, injection moulded and oxygen plasma modified PEEK implants in a sheep model, 2014 Biomaterials, 35(12), 3717-3728.
Poulsson et al. "Surface Modification Techniques of PEEK, Including Plasma Surface Treatment", 2019, In PEEK Biomaterials Handbook (pp. 179-201), William Andrew Publishing.
Rao et al. "Spine Interbody Implants: Material Selection and Modification, Functionalization and Bioactivation of Surfaces to Improve Osseointegration", 2014, Orthop. Surg., 6(2), 81-89.
Robotti et al. "Thermal Plasma Spray Deposition of Titanium and Hydroxyapatite on PEEK Implants", 2019, In PEEK Biomaterials Handbook (pp. 147-177), William Andrew Publishing.
Spece et al. "3D printed porous PEEK created via fused filament fabrication for osteoconductive orthopaedic surfaces", 2020, Journal of the Mechanical Behavior of Biomedical Materials, p. 103850.
Tan et al. "Fabrication and characterization of three-dimensional poly(ether-ether-ketone)/-hydroxyapatite biocomposite scaffolds using laser sintering", 2005, J. Eng. Med., 219, 183-194.
Torstrick et al. "Porous PEEK improves the bone-implant interface compared to plasma sprayed titanium coating on PEEK", 2018, Biomaterials, 185, 106-116.
Walsh et al. "Plasma-sprayed titanium coating to polyetheretherketone improves the bone-implant interface", 2015, Spine J., 15, 1041-1049.
Basgul et al. "Heat transfer-based non-isothermal healing model for the interfacial bonding strength of fused filament fabricated polyetheretherketone", Oct. 2021, Additive Manufacturing, Science Direct, vol. 26, 102097.
Manzoor et al. "3D printed PEEK/HA composites for bone tissue engineering applications: Effect of material formulation on mechanical performance and bioactive potential", Journal of the Mechanical Behavior of Biomedical Materials, Sep. 2021, vol. 121, 104601.
Zheng et al. "Effects of printing path and material components on mechanical properties of 3D-printed polyether-ether-ketone/hydroxyapatite composites", Journal of the Mechanical Behavior of Biomedical Materials, Jun. 2021, vol. 118, 104475.
PCT Notification of Transmittal of the International Search Report and the Written Opinion of the International Searching Authority issue to counterpart application PCT/US2021/050074 dated Dec. 20, 2021.

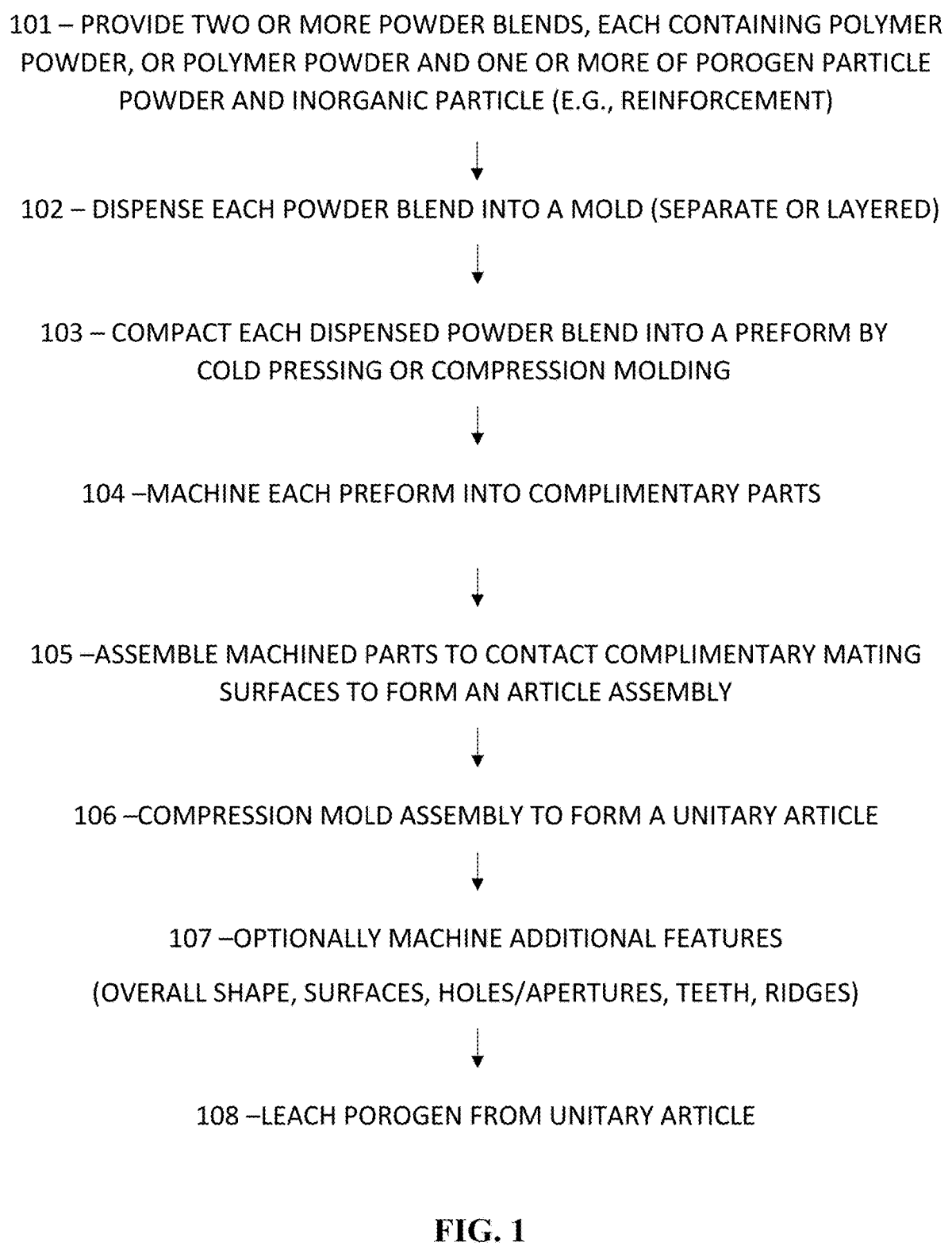

101 – PROVIDE TWO OR MORE POWDER BLENDS, EACH CONTAINING POLYMER POWDER, OR POLYMER POWDER AND ONE OR MORE OF POROGEN PARTICLE POWDER AND INORGANIC PARTICLE (E.G., REINFORCEMENT)

↓

102 – DISPENSE EACH POWDER BLEND INTO A MOLD (SEPARATE OR LAYERED)

↓

103 – COMPACT EACH DISPENSED POWDER BLEND INTO A PREFORM BY COLD PRESSING OR COMPRESSION MOLDING

↓

104 –MACHINE EACH PREFORM INTO COMPLIMENTARY PARTS

↓

105 –ASSEMBLE MACHINED PARTS TO CONTACT COMPLIMENTARY MATING SURFACES TO FORM AN ARTICLE ASSEMBLY

↓

106 –COMPRESSION MOLD ASSEMBLY TO FORM A UNITARY ARTICLE

↓

107 –OPTIONALLY MACHINE ADDITIONAL FEATURES (OVERALL SHAPE, SURFACES, HOLES/APERTURES, TEETH, RIDGES)

↓

108 –LEACH POROGEN FROM UNITARY ARTICLE

FIG. 1

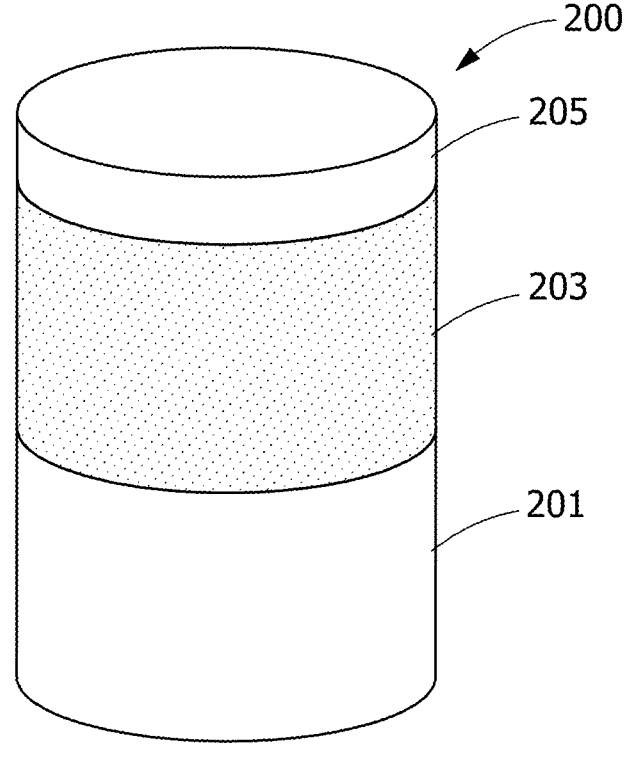
FIG. 2
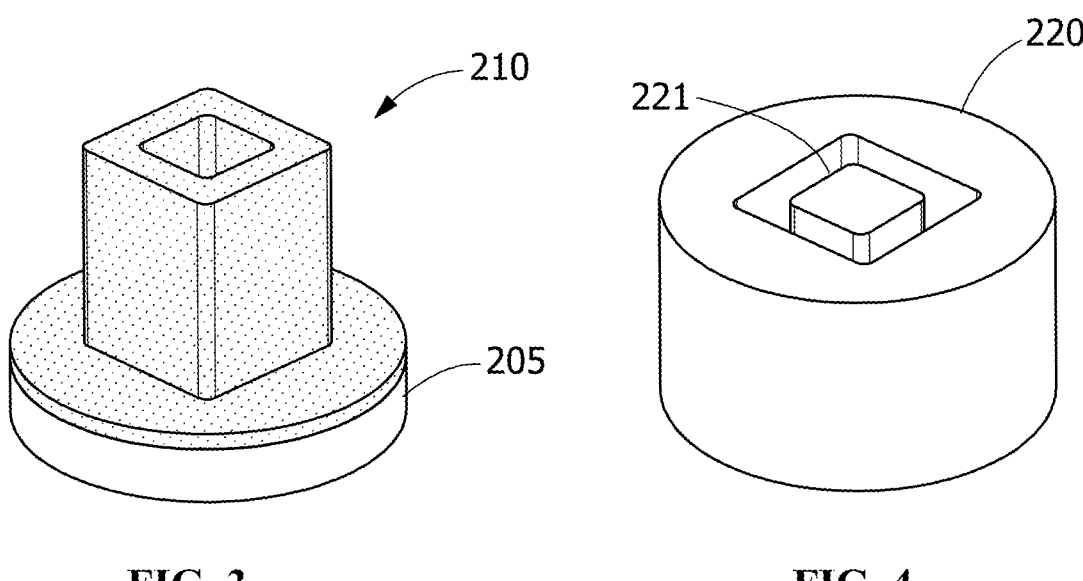
FIG. 3       FIG. 4

| | Left | Top | Right | Bottom | Left | Top | Right | Bottom |
|---|---|---|---|---|---|---|---|---|
| Mean | 2.22 | 2.01 | 2.06 | 2.06 | 1.65 | 1.65 | 1.86 | 3.73 |
| Std Dev | 0.01 | 0.06 | 0.03 | 0.04 | 0.23 | 0.45 | 0.14 | 0.25 |
| COV | 0.01 | 0.06 | 0.03 | 0.04 | 0.14 | 0.27 | 0.08 | 0.07 |

IMPLANTABLE MEDICAL DEVICE WITH VARIED COMPOSITION AND POROSITY, AND METHOD FOR FORMING SAME

CROSS-REFERENCE TO RELATED APPLICATIONS

This application claims the benefit of, and priority to, U.S. patent application Ser. No. 17/870,911 filed on Jul. 22, 2022 titled IMPLANTABLE MEDICAL DEVICE WITH VARIED COMPOSITION AND POROSITY, AND METHOD FOR FORMING SAME and issued as U.S. Pat. No. 12,005,616 B2 on Jun. 11, 2024, which is a continuation of claim priority to and benefit of U.S. patent application Ser. No. 17/473,385 filed on Sep. 13, 2021 titled IMPLANTABLE MEDICAL DEVICE WITH VARIED COMPOSITION AND POROSITY, AND METHOD FOR FORMING SAME and issued as U.S. Pat. No. 11,426,904 B2 on Aug. 30, 2022, and Application No. PCT/US2021/050074 filed on Sep. 13, 2021 titled IMPLANTABLE MEDICAL DEVICE WITH VARIED COMPOSITION AND POROSITY, AND METHOD FOR FORMING SAME, which claims benefit from U.S. Provisional Application No. 63/077,308, titled IMPLANTABLE MEDICAL DEVICE WITH VARIED DENSITY THERMOPLASTIC COMPOSITE BODY AND METHOD FOR FORMING SAME, which was filed on Sep. 11, 2020, and which are hereby incorporated by their reference in their entirety.

FIELD

The present disclosure relates generally to a method for forming thermoplastic devices having regions with varied material composition and/or porosity. In some embodiments, the devices are biomedical implants.

BACKGROUND

There are a variety of approaches that may be employed to manufacture implantable devices, e.g., for interbody spinal fusion and/or orthopedic implant fixation, from materials that have varied features, such as the material composition and porosity. Variations in material composition and porosity are desirable to promote bioactivity for bone on-growth along surfaces of implants and bone ingrowth into pores for biologic fixation, respectively. There are many deficiencies associated with existing state of the art approaches; the invention overcomes these deficiencies.

Described briefly, below, are a variety of present state-of-the-art manufacturing methods and brief description of at least some of their limitations.

The art includes descriptions whereby non-porous (dense) implants of a single material composition are machined from a solid material, such as extruded polyetheretherketone (PEEK) or hydroxyapatite (HA) reinforced PEEK (HA-PEEK) and cast titanium. Variations in features (material composition and porosity) and implant shapes are limited by traditional machining operations. Therefore, additional processing steps are required to create variations in material composition and porosity, but these additional steps inherently add cost and time to manufacturing. Specific additional processing steps and other limitations are described below.

The art also includes descriptions whereby line-of-sight surface modification processes are used to create variations in material composition and surface roughness. Thermal spray processes, such as those described in PCT Application WO2011004217 and U.S. Pat. No. 9,023,419, are used to add a coating of HA to PEEK or titanium implant surfaces, or titanium to PEEK implant surfaces, to promote bioactivity and bone on-growth. Media blasting, e.g., US Patent Application US20150018956A1, is used to prepare a roughened micro- or nano-topography on titanium to promote bioactivity and bone on growth. Plasma treatment, e.g., PCT Application WO2016097721, is used to alter the surface chemistry and nano-topography of PEEK for improved wettability. However, these line-of-sight surface modification processes do not permit bulk material modification and do not permit uniform modification of all material surfaces on a device, especially interior surfaces and internal pore surfaces. Furthermore, the coating-implant interface could be vulnerable to spalling (e.g., mechanical failure) or chemical degradation or resorption, thus potentially diminishing its utility. In addition, none of these processes are able to also create variations in microscale porosity suitable for bone ingrowth.

The art also includes descriptions whereby line-of-sight surface modification processes are also used to create variations in porosity. U.S. Pat. No. 9,085,665, U.S. Ser. No. 10/231,813, and U.S. Ser. No. 10/405,962 describe a process wherein a sacrificial porogen (e.g., salt) is pressed into external surfaces of PEEK implants to create a superficial surface layer of porosity. However, the layer of surface porosity is limited to 500 μm in depth and on the implant end plates only, as the process is limited to line-of-sight application to exterior implant surfaces. There was no disclosure of methods for creating porosity on internal surfaces of implants or simultaneous modification of PEEK to promote bioactivity. As with conventional PEEK implants, fibrous tissue is formed at the implant-tissue interface rather than direct apposition of bone.

The art also includes descriptions whereby solution-based and vapor-based surface modification processes are used to create variations in material composition and surface roughness. Chemical solution deposition processes, e.g., U.S. Pat. Nos. 6,569,489, 6,736,849, and PCT Application WO2010057949 have been used to deposit a superficial coating of HA on PEEK and titanium implant surfaces. Similarly, chemical solutions and vapors have been used to etch and/or oxidize titanium (e.g., U.S. Pat. Nos. 6,911,249, 8,496,710, 9,314,337, 9,131,995, 9,393,092, and 9,931,438, US Patent Application US20190192303, and PCT Applications WO2009029507 and WO2009009666) and PEEK (e.g., U.S. Ser. No. 10/117,966) implant surfaces, altering the surface energy and creating nanoscale topography. These processes are able to access all material surfaces, including interior surfaces and internal pore surfaces, and thus remedy the primary limitation of line-of-sight surface modification, but similarly do not permit bulk material modification. These processes are also subject to other limitations, such as the cost of high temperature and vacuum systems, hazards associated with solutions and vapors comprising strong acids (e.g., concentrated sulfuric acid) and organic solvents (e.g., methylene chloride). Moreover, none of these processes are able to also create microscale porosity suitable for bone ingrowth.

The art also includes descriptions whereby solution-based surface modification processes have been used to create variations in nanoscale porosity. U.S. Pat. No. 9,931,438 describes a process wherein a superficial layer of porosity is created on PEEK surfaces. However, both the pore size and superficial layer thickness is limited to <100 μm, whereas a pore size greater than 100 μm is known to be favorable for bone ingrowth. Additionally, the superficial layer of porosity is created by exposing PEEK to a potentially hazardous solution of concentrated sulfuric acid.

The art also includes descriptions whereby joining processes such as bonding, welding, and mechanical fastening are used to add a bioactive and/or porous material to implant surfaces. U.S. Pat. No. 8,562,685 and U.S. Ser. No. 10/413,427 describe interbody spinal fusion implants manufactured by joining titanium endplates to a PEEK substrate. U.S. Pat. No. 9,700,431 describes a process wherein porous titanium or PEEK is created by cutting holes into thin sheets of material which are assembled and bonded together. However, similar to coatings prepared by other processes described above, bonded or joined materials are prone to mechanical failure and/or chemical degradation at the interface(s). Joining processes also add time and cost to manufacturing.

In summary, all the above processes described in the art for modifying conventional machined titanium, PEEK, and HA-PEEK implants suffer from limitations in manufacturing time/cost, application to bulk material regions rather than surfaces or select-surfaces, and/or the presence of interfaces susceptible to failure.

In addition to the above, the art also includes descriptions whereby non-porous (dense) implants of a single or composite material composition can be injection-molded from pelletized material, such as PEEK or compounded HA-PEEK, respectively. US Patent Application US20140035201 describes compounding PEEK and HA in a twin-screw extruder to create pelletized material for injection molding. However, high shear flow of molten PEEK during extrusion and injection molding is known to cause HA particles to be encapsulated within the PEEK matrix and thus not exposed on as-molded surfaces. As such, bioactive HA particles are unable to provide bioactivity unless exposed by subsequent machining or surface abrasive processes. Additional limitations of this process include attrition of the HA particles and wear on the equipment, leading to nonuniformities and impurities. Finally, this process is not able to create variations microscale porosity without additional processing steps described above for machined implants.

The art also includes descriptions whereby dense and/or porous implants of a single material or composite material composition have been prepared by additive manufacturing (or 3D printing) of titanium powders, PEEK powders or PEEK filaments. U.S. Pat. Nos. 7,537,664, 8,728,387, 9,456,901, 9,180,010, and 8,590,157 describe titanium implants prepared by selective laser melting (SLM), selective laser sintering (SLS) and electron beam melting (EBM) from powder feedstock. PEEK implants have been prepared from powder feedstock by SLS and filament feedstock by fused filament fabrication (FFF) or fused deposition modeling (FDM). Each of these processes creates 3D materials by layer-by-layer assembly and are thus reliant upon adequate joining of subsequent layers. Mechanical properties are thus dependent on the build direction and typically diminished compared to equivalent material manufactured by bulk forming processes. For example, PEEK implants prepared by SLS and FFF/FDM exhibit decreased mechanical properties compared to machined or molded PEEK. In particular FFF/FDM has suffered from poor adhesion between subsequent build layers. Moreover, SLS and FFF/FDM are limited to relatively low porosity levels and challenges incorporating HA particles in the PEEK feedstock. SLS also suffers from high cost due to low production rates and high levels of waste powder feedstock. FFF/FDM have been used to prepared dense and/or porous HA-PEEK, but HA exposure is limited due to the formation of a polymer skin during extrusion of filament feedstock. Thus, while these processes are able to create variations in porosity, variations in material composition and/or surface topography require additional processing steps described above for machined implants. Finally, 3D-printed titanium implants still limit radiographic assessment of osteointegration similar to conventional titanium implants and can be prone to subsidence and stress shielding due to the high elastic modulus of titanium relative to adjacent bone.

The art also includes descriptions whereby porous implants of a single or composite material composition have been prepared by adding a sacrificial porogen to the material composition, forming the implant, and removing the porogen. U.S. Pat. No. 8,829,096 and PCT Application WO2011107803 describe a process wherein a packed bed of porogen particles is infiltrated with molten PEEK under pressure or infiltrated with particulate PEEK under vibration and subsequently heated, and the porogen is removed to create a porous PEEK construct. This process is not amenable to HA-PEEK compositions which exhibit higher melt viscosity. U.S. Pat. No. 8,383,024 describes a process of mixing salt particulate with PEEK powder, heating the mixture to a temperature where PEEK is molten but the porogen remains solid, molding under relatively low pressure ($<5$ MPa), and leaching the salt to create a porous PEEK construct. U.S. Pat. No. 10,945,854 was the first to disclose a process for creating porous HA-PEEK constructs by compression molding mixtures of PEEK, HA and salt porogen particulates, and leaching the porogen after molding to provide constructs wherein HA particles were both embedded within the PEEK polymer to act as a mechanical reinforcement and exposed on internal pore surfaces to promote bioactivity. According to the methods of both PCT Application WO2001054746 and PCT Application WO2007051307, variations in porosity and/or material composition require that a mold is filled with powder mixtures containing varying compositions and/or amounts of the porogen prior to molding. As more fully described in the examples herein, the instant inventors have shown that relative differences in the compaction or densification behavior of powder mixtures containing varying compositions and/or amounts of the porogen, combined with a need for precise dispensing of powder mixtures, poses challenges to forming constructions wherein regions of varied porosity or material composition exhibit precise dimensional tolerances and uniform shape.

In summary, all the above processes described in the art for manufacturing dense and/or porous implants of a single or composite material composition, viz. titanium, PEEK, or HA-PEEK, present deficiencies in terms of creating regional variations in both porosity and material composition, creating continuous microscale porosity within reinforced thermoplastics (e.g., HA-PEEK), and providing exposure of reinforcements on as-prepared surfaces. None of the above processes address challenges with molding constructs having regions with varied material composition and porosity.

The instant disclosure overcomes the deficiencies of the art as noted above.

BRIEF DESCRIPTION OF THE INVENTION

In one exemplary embodiment, a method according to the disclosure includes a series of forming and processing steps for rendering a single monolithic molded thermoplastic article comprising three-dimensional regions of varied material composition and/or porosity. In various embodiments, the formed article or device is employed as a biomedical implant and shaped according to its intended use, for example in the spine.

According to the method, the article comprises at least two regions and at least two of the two or more regions vary from one another with respect to material composition and/or porosity.

In another exemplary embodiment, an implantable medical device formed according to an inventive method includes providing a thermoplastic composite article having regions of varied material composition and/or porosity wherein the article is formed by first providing two or more powder blends comprising either polymer powder, or a blend of polymer powder with one or more of a porogen powder and an inorganic particle powder (e.g., reinforcement). The two or more powder blends are dispensed into molds and compacted into two or more preforms which are subsequently machined into parts for assembly.

In some embodiments, the preforms are compacted by compression molding at elevated temperature. In other embodiments, the preforms are compacted by cold pressing (also known as powder compacting).

In some embodiments, the preforms are formed simultaneously, for example, as layers in the same die or mold. In other embodiments, preforms may be formed separately, in two or more dies or molds. In either case, the dies or molds are unlimited by size or shape.

Compacted preforms are machined to provide at least two interfitting parts, the parts each comprising complementary mating surfaces. The machined parts are assembled to provide an article assembly that is in a further step compression molded to provide a unitary article that is free from discernible boundaries between the assembled interfitting parts.

In accordance with the disclosure, the methods hereof provide articles, for example, implantable medical devices having regions of varied material composition and/or porosity that include at least two porous regions that vary in porosity, wherein the porosity in at least one of the porous regions is continuous through the article between opposing surfaces, for example, upper and lower surfaces to define "through porosity."

Also, in accordance with the disclosure, the methods hereof provide articles having regions of varied material composition and/or porosity that include at least two porous regions that vary in porosity, wherein the porosity in at least one of the porous regions includes porosity exposed on one or both of interior surfaces and exterior surfaces of the article. In some such embodiments, the methods hereof provide articles wherein porosity in at least one of the porous regions is through porosity. In some such embodiments, the methods hereof provide articles wherein at least one of the porous regions includes exposed porosity on some but not all of one or both interior and exterior surfaces of the article. In some such embodiments, at least one of the porous regions includes porosity exposed on two or more opposing interior and/or exterior surfaces of the article (e.g., opposing or opposite sides), or on orthogonally oriented interior and/or exterior surfaces of the article, or both.

Also, in accordance with the disclosure, the methods hereof provide articles having regions of varied material composition and/or porosity that include at least two porous regions that vary in porosity.

Also, in accordance with the disclosure, the methods hereof provide articles having regions of varied material composition and/or porosity wherein the porosity in at least one of the porous regions has a thickness within the article that is greater than 0.5 mm, or greater than 1.0 mm, or greater than 2.0 mm.

In some particular embodiments, the methods hereof provide articles having regions of varied material composition and/or porosity that include at least two porous regions that vary in porosity wherein the porosity in at least one of the porous regions has a thickness within the article that is greater than 0.5 mm, or greater than 1.0 mm, or greater than 2.0 mm.

These and other aspects of the invention are set out in the appended claims and described in greater detail in the detailed description of the invention. This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning. It is to be understood that both the foregoing general description and the following detailed description are exemplary and explanatory only and are not restrictive of the disclosure.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

FIG. 1 is flow diagram that presents an embodiment of the inventive method.

FIG. 2 shows a first image in a sequence that illustrates forming inventive articles according to the steps of the method as shown in FIG. 1;

FIG. 3 shows another image in a sequence that illustrates forming inventive articles according to the steps of the method as shown in FIG. 1;

FIG. 4 shows another image in a sequence that illustrates forming inventive articles according to the steps of the method as shown in FIG. 1;

DETAILED DESCRIPTION OF THE INVENTION

Figure 5:
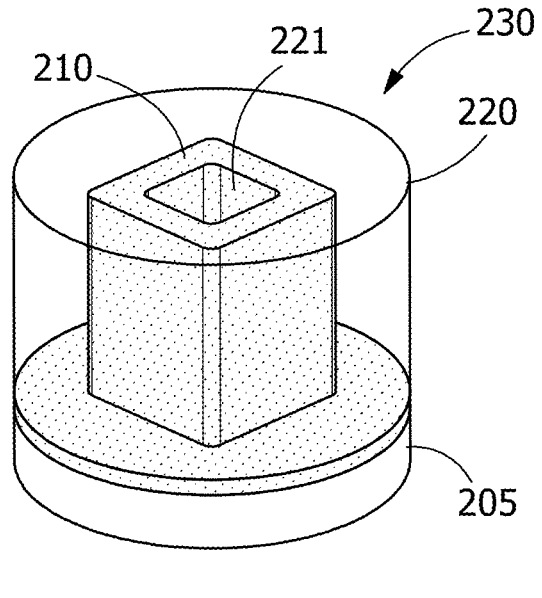
FIG. 5 shows another image in a sequence that illustrates forming inventive articles according to the steps of the method as shown in FIG. 1.

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

Provided are a method for making articles, for example, medical device implants, which have two or more regions that vary in one or more of porosity and composition, wherein, in some embodiments, at least one of the regions may be porous and one or more regions may include bioactive materials and at least two regions may vary in polymer composition, and combinations of these. In some specific embodiments, the method provides for articles that include two or more regions that vary in porosity. The invention also provides articles that may also vary in terms of the composition of thermoplastic polymer present in two or more regions. It will be appreciated that the disclosed method is not limited to any particular use or type of device, and while the examples herein provide an implantable biomedical device for use in the spine, other applications and uses are possible, including non-medical applications.

The articles formed according to the inventive method may be employed as medical device implants, and are useful for various purposes, in particular for orthopedic implants, and more particularly for use in the spine. Such medical device implants having varied regions address the mechanical and biological requirements for maximizing integration of the implant during bony fusion between vertebrae. In the various embodiments, each region of the formed articles may vary in material composition, for example, in the presence and/or amounts of one or more polymers, and in some embodiments in the presence and/or amounts of one or more of inorganic powders, which may function as mechanical reinforcements or bioactive fillers or both, and in some embodiments the presence and extent of porosity, and in some embodiments the extent and presence of other features that may be imparted according to the method, and combinations of these.

As noted above, in some particular embodiments, the articles provide medical device implants that have at least two regions that vary wherein one region is relatively more dense (i.e., is relatively less porous) and one region is relatively more porous than the other. In some embodiments, medical device implants formed according to the inventive methods take advantage of dense and porous reinforced polymer wherein the porosity (or relative density) of regions of the device may be varied to one or more of: match or approximate mechanical properties of vertebral bodies or bone tissue which is to be contacted by the implant; provide anatomically desirable distraction between adjacent vertebral bodies or bone tissue which is to be contacted by the implant; provide mechanical strength to support and maintain balance in the sagittal plane relative to vertebral bodies or bone tissue which is to be contacted by the implant; eliminate or minimize subsidence into vertebral bodies or bone tissue which is to be contacted by the implant; and provide placement of porous regions for optimal osteointegration.

The inventors hereof have recognized that to achieve variations in porosity and/or material composition using some of the conventional practices as described in the background hereof, a mold would typically be filled with component mixtures or blends, for example, powder mixtures or blends, containing varying compositions and/or amounts of one or more of a reinforcement material and a porogen prior to molding. In following this general approach using powder forms of polymer, reinforcement and porogens, the inventors recognized that the molded materials were deformed such that the regions of varied material composition and/or porosity in the final article exhibited distortion and nonuniformities relative to what was intended based on the powder blends and their placement in the molds. The inventors posited, without being bound by theory, that the problem of distortion was influenced by relative differences in the compaction and/or densification behavior of powder mixtures containing varying compositions and/or amounts of polymer, reinforcement and/or porogen, and challenges with precise dispensing of powder mixtures. The instant disclosure addresses those challenges.

According to the disclosure, the inventors have developed a method wherein parts (also referred to as regions) of a final article are first formed from raw material containing varying particulate powder blends of polymer alone (e.g., PEEK) and mixtures of polymer (PEEK), reinforcement (e.g., HA), and sacrificial porogen (e.g., NaCl). The method includes providing blends of powders of the polymer and polymer with reinforcement and/or porogen wherein each of at least two blends vary in terms of the content of these three particulate components, wherein all blends include one or more polymer powders, and at least one or more blends include polymer powder and one or more of reinforcement and porogen powder(s). The powders may be provided in dry form or wet (dispersed in a fluid that does not solvate any of the particulates). The powder blends are dispensed in molds, as further described herein below, and compacted into two or more preforms which are subsequently machined into two or more complementary parts. The complementary parts are assembled together with closely mating surfaces and the assembly is compression molded to form a monolithic article comprising regions of varied material composition and/or porosity that is free from discernible boundaries between the assembled parts. Each region of varied material composition and/or porosity in the final article exhibits accurate dimensional tolerances and uniform shape throughout the final article, without distortion and nonuniformities that may be caused by differences in the compaction or densification behavior of powder mixtures that are first dispensed directly into regions of the final article and then molded simultaneously. As such, the invention solves a known problem in the art of manufacturing thermoplastic composite biomedical implants having regions with varied material composition and porosity. In some embodiments, the preforms are compacted by compression molding at elevated temperature. In other embodiments, the preforms are compacted by cold pressing (also known as powder compacting). Thus, the disclosure contemplates that either compression molding or cold pressing may be employed to initially form the preforms that will be further machined into complementary parts and molded to provide articles according to the invention, and examples of each are described herein, and an exemplified article comprising preforms that were initially prepared by compression molding is specifically shown in the drawings.

As used herein, it will be appreciated that the term "powder blend" contemplates that only one powder may be present, i.e., polymer powder. Accordingly, a powder blend may be selected from the group consisting of powder of a single polymer, powders of two or more different polymers, powders of one or more polymers and at least one reinforcement, powders of one or more polymers and at least one porogen, and powders of one or more polymers, at least one reinforcement and at least one porogen. As further described herein, articles formed according to the inventive method include porous regions also referred to as scaffolds.

As used herein, the term "free from discernible boundaries" means that the final formed article is a unitary article comprising an essentially contiguous polymer matrix without any discernible gap between the assembled parts, though each part may be formed with different material composition (e.g., one or more of different polymers, different reinforcements, or other additives) or with different porosities. "Free from discernible boundaries" does not mean that there are no visible variations between adjacent regions, and it will be understood that it may or will be evident that adjacent regions have visually detectible differences due to the presence or absence or extent of porosity, reinforcement, or other combinations of features. What should be appreciated is that the inventive method hereof that involves assembling interfitting parts with close tolerances provides a final unitary article in which the toleranced gap between assembled parts no longer exists as a result of the inventive method.

Referring now to the drawings, FIG. 1 is a flow chart that sets for the steps according to the method, which are more specifically described as follows (references numerals from FIG. 1 shown in parentheses):

i. (101) Provide at least two powder blends, each powder blend including at least a polymer powder, and at least one powder blend including one or more of a porogen powder, and an inorganic particle powder (e.g., reinforcement), to provide at least two powder blends that differ from one another in terms of content of the porogen powder, or the inorganic particle powder, or both, the blends of powders selected to provide at least two parts that are obtained by heat and pressure molding or by cold pressing of each powder blend, the at least two parts different from one another in terms of one or more of porosity, polymer composition, inorganic particle composition, or both;

ii. (102) Dispense each of the powder blends into separate molds, or as two or more layers within the same mold, or a combination of these;

iii. (103) Compact each of the powder blends into preforms by compression molding or cold pressing, wherein when the powder blends are dispensed within the same mold, the compacted layers are mechanically separated (e.g., by machining) after molding;

iv. (104) Machine each preform into two or more complementary parts for assembly;

v. (105) Assemble the machined parts with complementary mating surfaces to form an article assembly;

vi. (106) Compression mold the article assembly to form a unitary article;

vii. (107) Optionally machine additional features in the article, including optionally machining the exterior surfaces of the formed article;

viii. (108) Leach porogen from unitary article.

It will be appreciated that the above method contemplates at least two powder blends for forming at least two preforms or complementary parts for assembly. In some embodiments, at least two powder blends may be provided for forming more than two preforms or complementary parts, for example, to form an article that is formed of three parts to provide an article that has three regions wherein two of those regions may be the same and those regions differ from the third region in terms of one or more of polymer composition, porosity and presence/amount of reinforcement. And in some embodiments more than two powder blends may be provided, for example three blends, which may be formed into at least three preforms or complementary parts that are used to form an article that has at least three discrete regions, wherein all of the regions are different from each other in terms of one or more of polymer composition, porosity and presence/amount of reinforcement.

As further described herein below, the molds or dies used for compacting powder blends into preforms or compression molding an article assembly into a unitary article may have any of a variety of possible sizes and shapes. While specific examples are provided and exemplified herein using a cylindrical mold, it will be appreciated that any size or shape mold may be used. Indeed, molds may be sized and shaped to form a single article or implant, or a mold may be sized and shaped to permit forming a plurality of machined parts for assembly (210, 220, 221) or article assemblies (230) that may be separated and machined to provide parts or articles, respectively, according to the invention. Further, while the instant disclosure exemplifies articles that include two assembled parts, it will be appreciated that more complex assemblies are contemplated wherein more than two discrete preforms or complementary parts may be formed, machined, and assembled according to the disclosure to form an article.

According to the above process, the mold conditions are as further described herein below. In some embodiments, according to step (i) above, the at least two powder blends are each dispensed into separate molds. In other embodiments, in particular employing dry powders, the powders may optionally be dispensed into a single mold in a layered fashion, as shown in FIG. 2. Thus, it will be appreciated that there may be two or more layers of powders dispensed in a layered or stacked configuration in a single mold. In accordance with layered embodiments, the method includes a further step of mechanically separating at least some of the layers after compacting the powder blends, which step may be referred to herein as a machining step. It will be appreciated that machining thus includes separating layers of preforms and also includes the steps of shaping preforms into discrete shapes that have complementary mating surfaces as described herein. Machining further includes rendering features on the surfaces of formed parts and articles as described herein.

Figure 6:
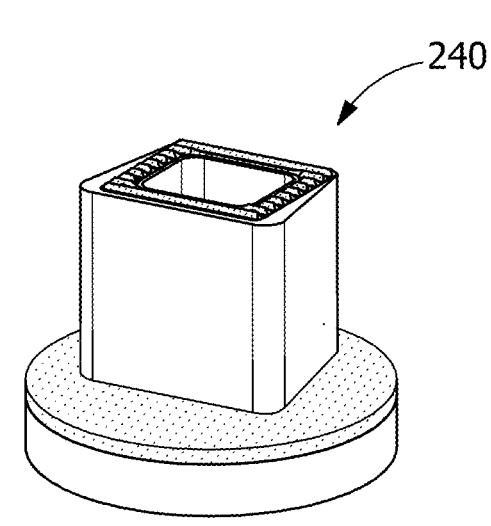
FIG. 6 shows another image in a sequence that illustrates forming inventive articles according to the steps of the method as shown in FIG. 1.
Figure 7:
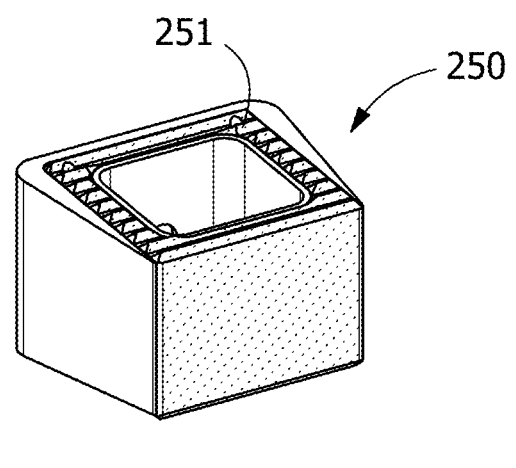
FIG. 7 shows another image in a sequence that illustrates forming inventive articles according to the steps of the method as shown in FIG. 1.
Figure 8:
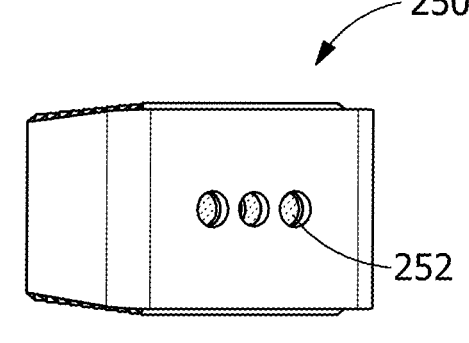
FIG. 8 shows another image in a sequence that illustrates forming inventive articles according to the steps of the method as shown in FIG. 1.

Referring again to the drawings, FIG. 3 and FIG. 4 each shows as an example, two intermediate forms of parts that are provided for assembly according to step (v), wherein the drawing represents parts formed from adjacent layers of the compacted powder preform represented in FIG. 2. As depicted in FIG. 3 and FIG. 4, each of the complementary parts of the intended article have been machined from the layers shown in FIG. 2. Referring now to FIG. 5, these parts are depicted as assembled, wherein the drawing shows the assembly as partially transparent to demonstrate the complementary shapes and respective mating surfaces of each of the parts as they were separated and then machined using the separated adjacent layers of the compacted powder preform represented in FIG. 2. Referring now to FIG. 6-FIG. 8, the parts as described from the drawings are depicted as compression molded into a unitary article and shown in three sequential images with some refined features machined onto the upper face (FIG. 6), lower face (FIG. 7) and back side (FIG. 8) of the article. Any machining according to optional step (vii) of the above-described method may include surface smoothing, texturing, application of features such as teeth, creation of holes or voids within individual parts or through more than one part. Referring to FIG. 6, the drawing shows regions of the compression molded unitary article as including a polymer and porogen base that is a possible feature of the layered molding represented in FIG. 2. Of course, it will be appreciated that whether initially compacted separately or in layers, the depicted base may or may not be included and is strictly determined based on the selected layering of powders and any intermediate separation of compacted layers prior to machining to form parts from the layers.

Referring again to the drawings, FIG. 9 is a schematic that shows certain representative steps of forming an article that represents an interbody spinal fusion implantable device according to the above-described process, wherein the article is formed of parts that are formed in a layered mold as represented in FIG. 2. It will be appreciated that the descriptive text is representative of but one embodiment of the method as shown in FIG. 1 and described herein above, and specifically represents the exemplified method described herein below as "Example of Forming Process."

According to the various embodiments, thermoplastic polymers are selected which can tolerate being melted multiple times with minimal effect on the material and are capable of melting and reflowing during the compression molding step (vi) of the article assembly to minimize or eliminate any boundary between the complementary parts.

Also, according to the various embodiments, the porogen typically has a higher melting temperature than the one or more polymers, such that the porogen does not melt and flow when the polymer is melted and flows around the porogen. In some embodiments, the porogen could be molten at the temperature used for compression molding the two or more polymers, provided that porogen is not decomposed at such temperature. In accordance with various embodiments, the reinforcements, for example comprising bioactive elements, can vary from 0 to 99% by volume in each powder blend, and the porogen powder can vary from 0 to 99% by volume in each powder blend, wherein each powder blend includes at least one reinforcement or porogen powder present from 1-99% by volume.

According to some particular embodiments, the powders may be provided wherein the powder blends may vary in terms of the polymeric powder. According to such embodiments that include powder blends with different polymers, the polymers included in the powders that will form adjacent parts will be of suitable chemical compositions that are at least partially miscible, such that melting and reflowing allow for the polymers in the adjacent parts to mix or bond at their mating surfaces during the compression molding step (vi) to provide an article with minimal or no boundary conditions between the adjacent parts.

According to the above process, the inventors have provided a novel solution to address the deficiencies in the art that allows for controlled shaping of molded polymer parts from raw material that contains selected sacrificial porogen and an inorganic particle powder. The inorganic powder may serve as a mechanical reinforcement, bioactive filler or both, for example, bioactive HA particles or whiskers. Articles formed according to the method overcoming deficiencies in the existing art, for example: parts can be formed without dimensional limitations as to the shape or volume of the shaped regions that are fit together; and gaps and voids between parts are completely filled when the shaped regions are assembled and molded together. According to some particular embodiments, final implant shape forming and features may be created by traditional subtractive manufacturing techniques once the region consolidation is completed and before the porogen is removed from the porous regions.

The inventors have demonstrated favorable results in forming articles with regions of varied porosity according to the above method, wherein the following assembly steps were followed, whereby the inventors:

i. Compacted two powder blends into preforms by either compression molding or cold pressing, each of which has the desired mixture of thermoplastic material, inorganic bioactive material and porogen that has a higher melting temperature than the thermoplastic material.

ii. Machined the preforms into complementary parts in a manner that they fit together with minimal gaps.

iii. Heated the article assembly above melting temperature of the polymer while providing mechanical constraint to resist volumetric expansion during heating and the melting phase of the polymer.

iv. In a first embodiment, cooled the heated article assembly to just below the melting point of the polymer, while applying an elevated pressure before reaching the polymer melting temperature, to mold the article into a monolithic body, and in a second embodiment, cooled the heated article assembly to just below the melting point of the polymer, while applying an elevated pressure after reaching the polymer melting temperature, to mold the article into a monolithic body.

v. Formed physical features in the monolithic article by machining to provide an implantable device.

vi. Cleaned the implant, removed the porogen, and packaged for sterilization.

According to the various embodiments, the compression molding temperature is an elevated temperature sufficient to melt and fuse polymer particles or parts with minimal damage to the reinforcement particles and, thus, may be any suitable temperature in the range from about 20° C. to about 450° C. including, but not limited to between 100° C. to about 400° C., alternatively between 100° C. to about 200° C., alternatively between 150° C. to about 250° C., alternatively between 200° C. to about 300° C., alternatively between 250° C. to about 350° C., alternatively between 300° C. to about 400° C., alternatively between 350° C. to about 450° C. Of course, it will be appreciated by one of ordinary skill that thermoplastic polymers may be molded at a temperature above the glass transition temperature and below the thermal decomposition temperature. Thus, in accordance with the various embodiments, the temperature for compression molding is in the range (° C.) from and including 20 to about 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440 to 450° C. including increments and ranges therein and there between.

The compression molding pressure may be applied at any point in time after heating above the melting temperature of the polymer and up to and through cooling to a temperature below the melting temperature but above the glass transition temperature of the polymer.

The powder compacting or compression molding pressure may be any suitable pressure, including, but not limited to, greater than at least 5 MPa, or at least 10 MPa, or at least 15

MPa, or at least 20 MPa, or at least 25 MPa, or at least 30 MPa, or at least 35 MPa, or at least 40 MPa, alternative at least 45 MPa, or at least 50 MPa, or at least 55 MPa, or at least 60 MPa, or at least 65 MPa, or at least 70 MPa, or at least 75 MPa, or at least 80 MPa, or at least 85 MPa, or at least 90 MPa, or at least 95 MPa, or at least 100 MPa, or at least 150 MPa, or at least 200 MPa, or at least 250 MPa.

In some particular embodiments, including as exemplified herein, the powder compacting or compression molding pressure may be in a range from about 100 MPa to about 300 MPa, and more specifically from about 125 MPa to about 250 MPa.

In some embodiments, the first compression molding of the two or more powder blends into a preform, and/or the second compression molding of complementary parts into a unitary article, may include a layer of polymer and porogen powder placed at both the top and bottom of the mold. The powder blend (or mixture) in these layers may comprise at least 50% porogen by volume and up to 99% by volume, or at least 70% by volume. The addition of these layers is advantageous in preventing flash of the molten polymer, and in maintaining accurate dimensional tolerances and uniform shape of regions with varied material composition and/or porosity throughout the final article, without distortion and nonuniformities that may be caused by differences in the compaction or densification behavior of powder mixtures, especially that caused by polymer flash.

In one embodiment, following simultaneously molding the first powder mixture and the second powder mixture, subtractive manufacturing (i.e., material removal) is utilized to form the net shape of the article (also referred to as a thermoplastic composite body) prior to leaching the porogen material from the at least one proto-porous portion.

Figure 9A:
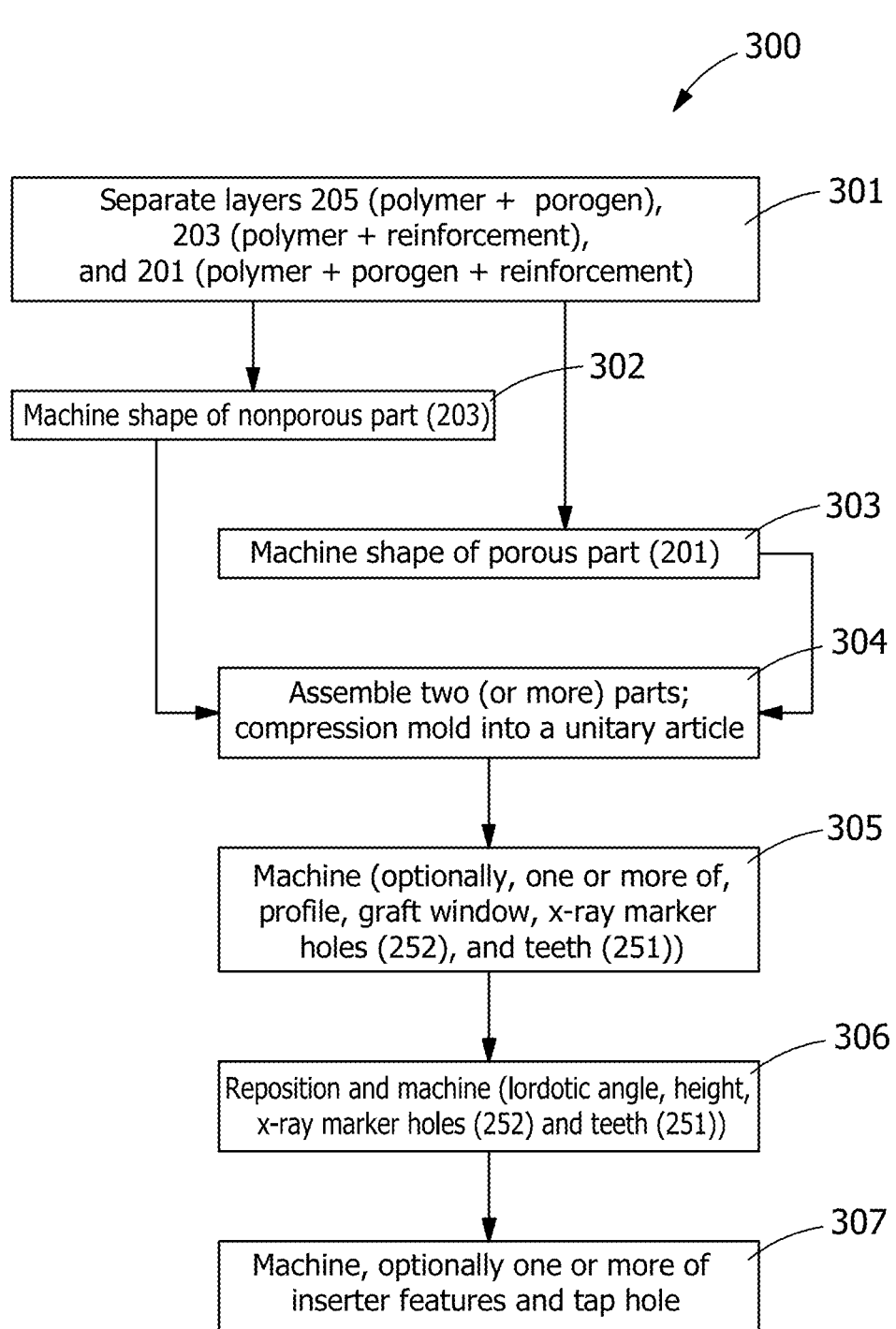
FIG. 9A is a flow diagram that shows an exemplary stepwise process for forming an implantable medical device wherein regions of the final article vary in material composition and/or porosity, according to embodiments of the disclosure.
Figure 9B:
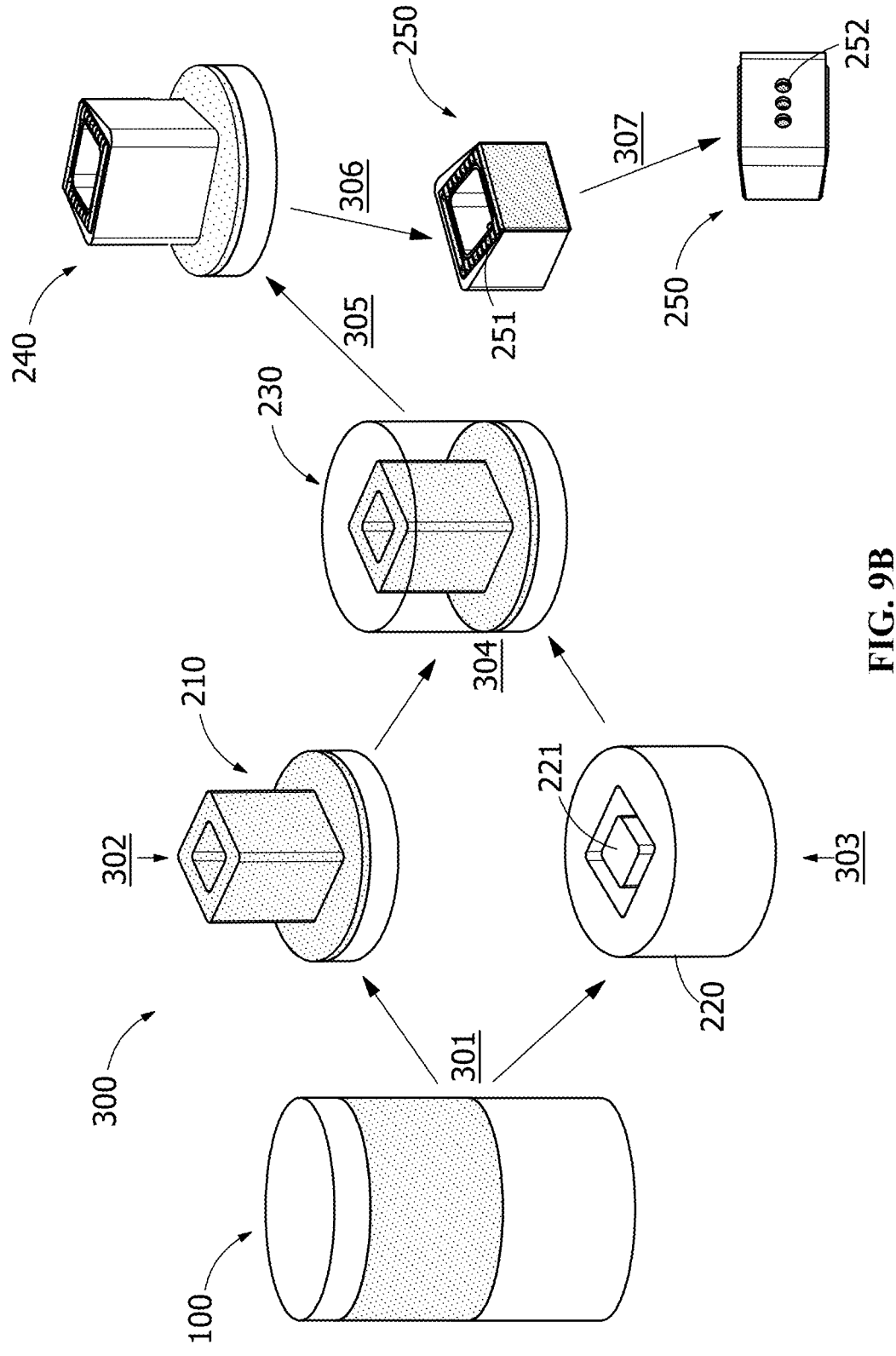
FIG. 9B is a schematic that corresponds with the stepwise forming process shown in FIG. 9A; and, FIG. 10 shows on the left side a schematic for cross sectioning an inventive article, and a series of photographic images of cross-sections and measured dimensions of discrete regions of articles varied material composition and/or porosity, the photographic images on the left representing an article formed by an exemplary embodiment of the inventive method, and the photographic images on the right representing an article formed by a method according to the prior art as described in the background herein.

Example of Forming Process:

Referring now in particular to FIGS. 9A and 9B, the described and schematically depicted process was followed for forming an implant wherein the polymer powder included PEEK, the reinforcement powder included HA whiskers, and the porogen powder included NaCl. Of course, it will be understood that one or more different suitable polymers powders may be selected, and likewise, one or more different reinforcement and porogen powders may be selected. FIG. 9A shows various steps 301-307 that describe various steps according to an exemplary embodiment of the invention, the embodiment directed to forming an article that includes at least one porous and at least one dense region. The steps are further illustrated in the schematic of FIG. 9B, which graphically illustrates the steps as described in FIG. 9A. According to that described embodiment, the following more detailed descriptions are merely representative of possible embodiments according to the disclosure, and it will be appreciated that other combinations of powder blends and components may be selected, and other forming and processing parameters may be employed, consistent with the disclosure. Referring to FIGS. 9A and 9B, according to the Part forming process below, the step xiv corresponds to the first step in the process (300) shown in FIG. 9A and FIG. 9B.

Part Forming Process:

i. Dry and sift HA whiskers, a NaCl porogen, and PEEK powder to eliminate powder agglomerates;

ii. Prepare a NaCl, HA and PEEK powder mixture by volume and store in drying oven;

iii. Prepare a HA and PEEK powder mixture by volume and store in drying oven;

iv. Dispense a volume of the NaCl, HA and PEEK (referenced as 201 in FIG. 2) powder mixture into a cylindrical mold that will become the porous region of an implant. Compress uniaxially at incrementally higher pressure, to a final pressure of 125 MPa or up to 250 MPa and hold final pressure for about one minute;

v. Dispense a volume of the HA and PEEK (referenced as 203 in FIG. 2) powder mixture into a cylindrical mold on top of the compacted NaCl, HA and PEEK (201) mixture. This will become the dense strut region of an implant. Compress uniaxially at incrementally higher pressure, to a final pressure of 125 MPa or up to about 250 MPa and hold final pressure for about one minute;

vi. Repeat Steps (iv) and (v) if it is desired to mold multiple porous and dense strut regions at one time;

vii. Dispense a volume of a NaCl and PEEK (referenced as 205 in FIG. 2) powder mixture in the top of the cylindrical mold, on top of the compacted HA-PEEK (203) mixture, which will form a minimum of a 2 mm thick layer once consolidated;

viii. Compact the entire volume (referenced as 200 in FIG. 2) at 125 MPa or up to about 250 MPa for 15 minutes at room temperature;

ix. Constrain the entire volume (200) in a press by positioning the compression piston in contact with the top at minimal pressure, or in some embodiments at a pressure of up to about 50 MPa to achieve volume constraint;

x. Heat to a temperature that is from about 350 C.±5° C. to about 375° C.±5° C.; then cool to 330° C.±5° C. and hold temperature;

xi. Compress uniaxially at 100 MPa or up to about 250 MPa for 45 minutes, in some embodiments the compression being applied before or after the material reaches the polymer melt temperature; then ramp down temperature at 40° C./hour;

xii. After one hour (or temperature below 300° C.) remove pressure and continue temperature ramp at 40° C./hour until the temperature is below 150° C.;

xiii. Eject part from the mold; and xiv. Section the dense HA-PEEK (203) region from the NaCl-HA-PEEK (201) regions.

The Dual Density Implant forming process below includes variation on the steps described above and includes steps 302-307 as exemplified in FIG. 9A and FIG. 9B.

Dual Density Implant Forming Process:

i. Machine the HA-PEEK region into a shape (referenced as 210 in FIG. 3) with nominal dimensions desired (302);

ii. Machine the NaCl-HA-PEEK (referenced as 220 and 221 in FIG. 4) region into a complementary shape with 0.05 mm nominal clearance per side (303);

iii. Assemble the complementary machined shapes together (referenced as 230 in FIG. 5) and place inside a mold cavity matching the shape of the article assembly (304);

iv. Ensure there is at least a 2 mm thick region of NaCl-PEEK above and below the HA-PEEK part. If there is not, add sufficient loose NaCl-PEEK volume to make this layer and compress uniaxially at 125 MPa;

v. Repeat Steps (i) through (iv) if it is desired to mold multiple article assemblies at one time;

vi. Compress uniaxially at 125 MPa or up to about 250 MPa for at least one minute and up to or more than 15 minutes at room temperature;

vii. Constrain the stack in a press by positioning the compression piston in contact with the top at minimal pressure, or in some embodiments at a pressure of up to about 50 MPa to achieve volume constraint;

viii. Heat to a temperature that is from about 350 C.±5° C. to about 375° C.±5° C.; and maintain at that temperature for about 10 to about 20 minutes, then cool to 330° C.±5° C. and hold temperature;

ix. Compress uniaxially at 100 MPa or up to about 250 MPa for 45 minutes, in some embodiments the compression being applied before or after the material reaches the polymer melt temperature; then ramp down temperature at 40° C./hour;

x. At temperature below 300° C., decrease pressure to 50 MPa and continue temperature ramp at 40° C./hour until temperature is below 150° C.;

xi. Eject from the mold;

xii. If step (v) is employed, separate the multiple article assemblies from each other;

xiii. Finish machine features for implant, optionally laser mark, optionally insert radiographic markers, remove salt porogen, clean, and package for sterilization (305, 306, 307) the unitary article (referenced as intermediate machined article 240 in FIG. 6 and final article 250 as in FIG. 7 and FIG. 8).

It will be appreciated that the foregoing process examples of the inventive method include process steps that are representative and that various parameters, including but not limited to the time, temperature and pressures may be varied. The inventors provide herein exemplified assemblies and articles formed by the above listed process steps, including formation of such articles specifically employing the above parameters, including but not limited to the time, temperature and pressures. However, the foregoing process steps are not intended to be limiting, and other parameters and variations of time, temperature and pressures are possible according to the broader disclosure.

In addition, it will be appreciated that while the foregoing process examples describe use of a cylindrical mold, other mold shapes may be selected, and suitable molds are not limited by size or shape. Further, it will be appreciated that finishing steps may be varied and one or more of the identified finishing steps need not be completed to provide a final article suitable for use as an implant.

Figure 10:
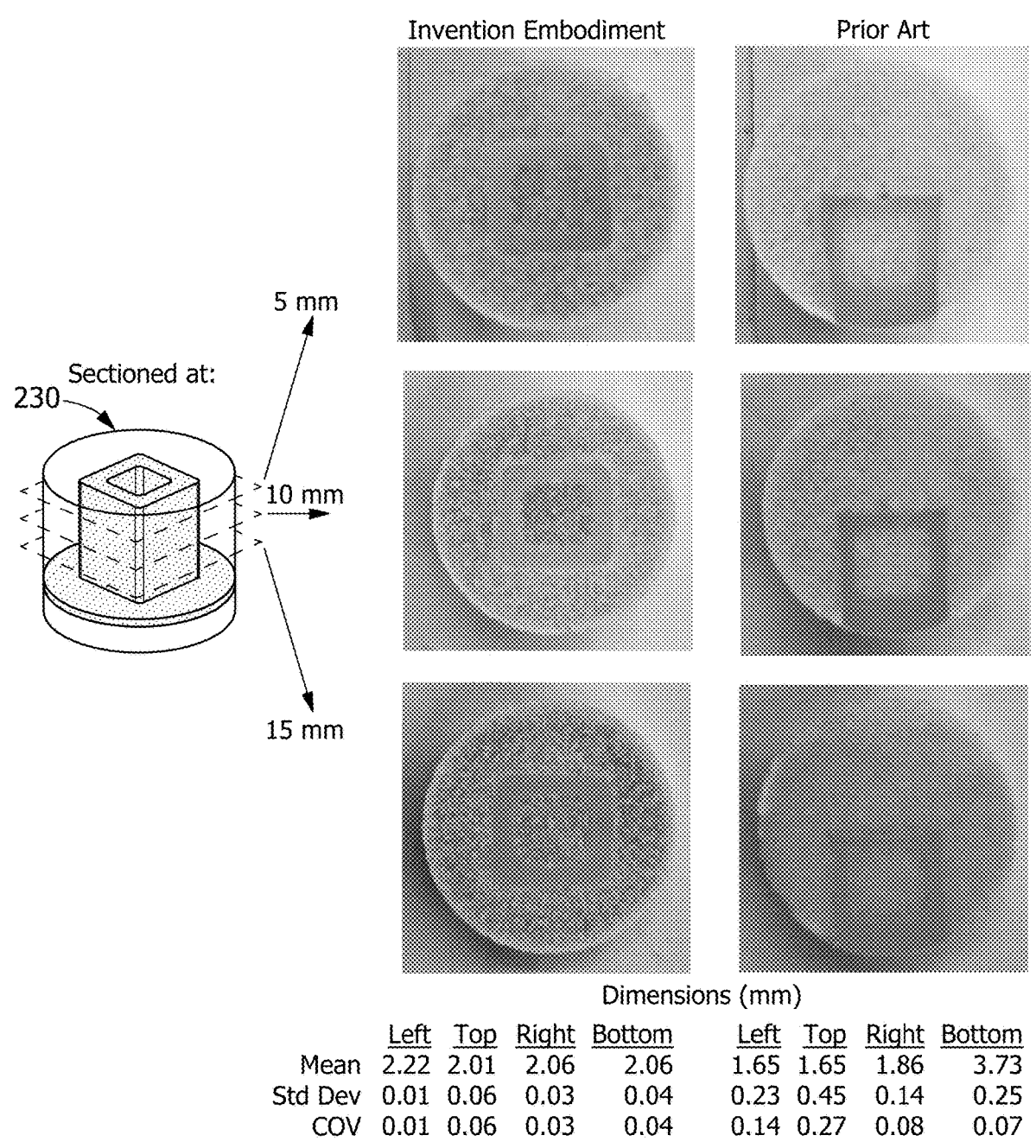

Referring again to the drawings, FIG. 10 provides an example of an article formed according to the disclosure (left side photographic images indicated as "Invention Embodiment," wherein the article was formed according to the foregoing inventive method, wherein preforms for the complementary parts were formed by compression molding at about 375° C.±5° C. and 250 MPa in a single mold in a stacked configuration as generally described above, and the article assembly was compression molded at about 375° C.±5° C. and 250 MPa, both while employing a minimal pressure to the compression piston during heating to achieve volume constraint.

Referring to FIG. 10, as shown in relation to an article formed by a prior art method, the inventive embodiment demonstrates significantly improved dimensional control of the molding of the respective porous and dense regions. As shown in FIG. 10, molding by the prior art method provided significant variation in the dimensional features (top, left, right, bottom) of the dense portion based on measurements taken from three 5 mm layers slices from the top to the bottom of the formed article.

Referring again to the drawings, the article as formed by the inventive method according to FIGS. 2-9 and as more specifically described above in relation to FIG. 10, was evaluated for its mechanical properties. Two samples of the article, each measuring 15×12×14 mm, were tested in static axial compression in displacement control at 12 mm/min following methods outlined in ASTM F2077.

TABLE 1

| Static axial compressive mechanical properties | | | |
|---|---|---|---|
| Specimen | Stiffness (kN/mm) | Yield Force (kN) | Yield Displacement (mm) |
| 1 | 14.8 | 7.1 | 0.6 |
| 2 | 18.5 | 10.3 | 0.7 |

The static axial compressive test results demonstrate that the implants remain intact and resist failure, particularly at the interface between the adjacent dense and porous regions which would be expected to be most vulnerable to failure if assembled according to conventional prior art methods.

Sample articles as described above were further submitted to dynamic axial compression following methods outlined in ASTM F2077. A maximum cyclic force of 1500 N was applied to each specimen at a constant frequency of 5 Hz. The forces were maintained at a constant sinusoidal waveform in amplitude control at a constant force ratio (R=min/max) equal to 10. Testing was terminated when the specimen reached the endurance value of 5,000,000 cycles without failure. As with the static testing, these results demonstrated that the articles withstand a clinically relevant fatigue loading without failure at the interface between the adjacent dense and porous regions.

Sample articles as described above were further submitted to static subsidence testing. Two implants measuring 15×12×14 mm were tested in static axial compression in displacement control at 6 mm/min to 10 mm to quantify load-induced subsidence into grade 15 (ASTM F1839) polyurethane foam test blocks following methods outlined in ASTM F2267. As used herein, "block stiffness" is a measure of how readily an implant subsides into adjacent bone superior and inferior to the implant upon loading in axial compression, as set forth in ASTM F2267. As known by one skilled in the art, a higher block stiffness indicates a greater resistance to subsidence, whereas a lower block stiffness indicates a lesser resistance to subsidence.

TABLE 2

| Static subsidence testing | | | |
|---|---|---|---|
| Specimen | Block Stiffness (N/mm) | Yield force (N) | Yield Displacement (mm) |
| 1 | 1068 | 1010 | 2.0 |
| 2 | 1046 | 948 | 2.0 |

The static subsidence test results indicate an unexpected subsidence resistance of the implants. The measured block stiffness is about 2.5-times greater than that reported as the median of conventional PEEK implants and nearly 300 N/mm greater than that reported as the 95th percentile of conventional PEEK implants (Peck et al., J. Biomechanics, 2017), which are already known to be subsidence resistant compared with metallic implants as described further below.

In an alternate embodiment, the inventors have prepared an article that was formed according to the foregoing inventive method, wherein the powder mixtures were compacted into preforms by cold pressing at about 250 MPa in a single mold in a stacked configuration or separate molds as generally described above, and during the compression molding of the article assembly, heating to about 350 C.±5°

C. to about 375° C.±5° C. while employing a minimal pressure of up to about 50 MPa to the compression piston during heating to achieve volume constraint.

Implants Formed According to the Method:

Articles formed according to the inventive method are, in some embodiments, biomedical implants, for example, interbody spinal fusion implants. Interbody spinal fusion is used to alleviate pain caused when a herniated, bulging, or flattened intervertebral disc impinges on the spinal cord or nerve root. The disc and vertebral endplates are removed, and an interbody fusion implant is inserted in the disc space to restore vertebral height, promote fusion of bone tissue between adjacent vertebrae, and thus, mechanically stabilize the spine.

Generally, the choices for spinal implants fall largely into metallic, polymeric, carbon fiber based and ceramic. Polyaryletherketone (PAEK) and bioactive PAEK composites for biomedical devices present several advantageous properties. PAEK polymers are generally biocompatible, bioinert, and radiolucent, and they exhibit a high strength and similar compliance to bone. One example of PAEK polymers used for biological implants is polyetheretherketone (PEEK). PEEK implants have many attractive characteristics, in particular for spinal surgeons and patients. Because of the radiolucency of PAEK composites, implants formed with PEEK allow post-operative radiographic assessment of fusion, which is problematic with metallic implants due to relatively high x-ray attenuation of titanium. PEEK also exhibits a modulus of elasticity similar to bone, enhancing load transfer and osteogenic signals to tissue in the implant, and reducing the likelihood of vertebral subsidence compared to alternatives formed with metals and ceramics. Porous PEEK provides surface area and architecture to support more extensive bony tissue ingrowth into the porous implant regions.

Of particular interest are porous PEEK materials that are reinforced with calcium phosphate, and in some examples, calcium phosphate particles selected from anisometric hydroxyapatite particles. These materials have been reported to provide bioactivity for enhanced bony ingrowth into the implant by the exposure of the anisometric hydroxyapatite particles on the surfaces of and extending within the pore voids. Despite the advantages of the foregoing described implant technologies, there remains a need in the art for implants that include the advantageous features of PAEK materials provided in an implant article that is adapted to spinal anatomy to achieve extensive bony ingrowth into the implant and provide mechanical properties that discourage stress shielding and have strength properties to handle the physiological loads during fusion.

Implants as provided according to the inventive method include a combination of dense and porous regions that influence the overall stiffness of the implant, wherein stiffness may be determined by the ratio of cross-sectional area (normal to direction of loading) of the portions of the implant that include porous and dense material. The ratio of cross-sectional area (normal to direction of loading) and placement of the dense and porous portions may be configured to provide an implant that can be matched to the mechanical properties of the vertebral bodies or bone tissue which it is intended to contact, both in overall implant stiffness, and in cross-sectional location of the relatively stiffer dense portions and the relatively flexible porous portions. In some embodiments, one or more of the dense and porous portions comprise one or more reinforcement particles which may be exposed on the surface of pores within at least some of the porous portions. In some particular embodiments, the implant is formed of a polymer selected from PAEK polymers, and include reinforcement particles in at least some portions, wherein the reinforcement particles comprise calcium phosphate compositions known to be bioactive.

Advantages realized according to the various embodiments of implantable devices that are adapted for use in the spine, as described herein, include the following: dense portions, for example those that comprise hydroxyapatite reinforced PEEK, provide biomechanical support only where it is needed; porous regions, for example those that comprise porous hydroxyapatite reinforced PEEK, enable bone ingrowth for osteointegration where most beneficial, for example on the inner implant surface in the graft window for graft incorporation to the implant and/or the anterior and lateral outer implant surface to support sentinel-sign bone growth; interconnected porosity provides biological pathway from vertebrae to vertebrae, through the implant to promote thorough osteoconductivity; in some embodiments, exposed reinforcements, for example, any bioactive reinforcement, and in some specific examples, hydroxyapatite whiskers, enhance bioactivity of the implant; porous fusion anteriorly supports sentinel-sign bone growth; porous fusion laterally maximizes the breadth of bone growth stabilization as well as adds a conformable material in a region where the bony geometry is less planar; dense material on the posterior outer implant surface discourages bone growth and maximizes mechanical support to maintain foraminal height; threaded inserter hole transmits inserter impaction to a load bearing frame; keystone or anatomic footprint allows for maximal endplate area contact while maintaining clearance for nerve pathways.

It will be appreciated that in some embodiments, the thermoplastic polymer may be a polymer other than PEEK and other than a PAEK polymer. It will also be appreciated that in some embodiments, the thermoplastic polymer may not include any reinforcement material within any one or more of the dense and porous portions, and that in yet other embodiments, the thermoplastic polymer may contain one or a combination of reinforcement materials that may or may not comprise calcium phosphate, hydroxyapatite or hydroxyapatite whiskers. In some examples, other bioactive reinforcements that do not comprise calcium phosphate may be selected.

Human bone tissues exhibit substantial variation in mechanical properties depending on the tissue density and microstructure. The properties are highly dependent on anatomic location and apparent density of the measured specimen. For example, cortical bone, such as in a thin outer wall of a vertebral body, has a relative porosity on the order of about 5-15% by volume, and a trabecular bone, such as in the central majority or marrow cavity of a vertebral body, has a porosity on the order of about 75-95% by volume. Due to the highly significant porosity differences, trabecular bone exhibits significantly lower effective mechanical properties compared to cortical bone. Therefore, depending on the application, synthetic composite materials for use as scaffolds and/or spinal fusion implants or other implant devices should possess the mechanical properties exhibited by cortical bone or trabecular bone, but must also have effective porosity to promote bone ingrowth.

To avoid the mechanical mismatch problems, such as stress shielding, it is desirable to substantially match or mimic the mechanical properties (e.g., elastic modulus) of the adjacent and/or substituted bone tissue. Several factors may be varied during the manufacturing of the implant device, and/or composite material and scaffold of the implant device, to tailor the mechanical properties including the ratio of the cross-sectional area of dense to porous thermoplastic polymer in the implant, the reinforcement volume fraction, aspect ratio, size and orientation; the polymer; and the size, volume fraction, shape and directionality of the porosity. Tailoring the mechanical properties of the implant and/or composite materials and scaffold reduces the likelihood of mechanical mismatch leading to a decreased risk of subsidence, stress shielding, bone resorption and/or subsequent failure of adjacent vertebrae.

Porous polymer scaffolds may be tailored to mimic biological and mechanical properties of bone tissue for implant fixation, synthetic bone graft substitutes, tissue engineering scaffolds, interbody spinal fusion, or other orthopedic applications. An example porous composite material described herein reduces subsidence and/or bone resorption resulting from mechanical mismatch problems between a synthetic scaffold of an implant device and the peri-implant tissue. Additionally, porosity and/or the pore sizes of the example thermoplastic composite are tailorable to specific applications to effectively promote the vascularization and growth of bone in the pores and/or void spaces of the example scaffolds, thereby improving bonding between the scaffolds and peri-implant tissue.

Composite materials or scaffolds may be synthesized or made through a process that enables reinforcement particles to be integrally formed with or embedded within polymer matrices. In this manner, the polymer matrices embedded with the reinforcement material may provide improved material properties (e.g., elastic modulus, fatigue strength, and toughness). The reinforcement particles may also be exposed on a surface of the matrices, which promotes bioactivity and/or osteointegration. Additionally, the process provides flexibility to tailor the level of reinforcement particles and porosity for a desired application. For example, a porogen material may be used to vary the porosity, while the pore size is tailored by, for example, sieving the porogen to a desired size. An additional pore tailoring method is to reshape a porogen material from it native shape to one that promotes interparticle contact between porogen particles and thus improved permeability. For example, sodium chloride particles are natively cubic. A process such as passing the particle through an energy source so that is melts and reforms to a shape other than its native cubic shape. Alternative shapes may be fibers, polyhedrals, spheres, spheroids, ellipses, ellipsoids, or any other suitable shape.

By varying the volume fraction of the reinforcement particles and the porosity of the example scaffold, the mechanical properties (e.g., elastic modulus) of the example scaffold of the implant device may be tailored to match those of the adjacent peri-implant bone tissue to reduce mechanical mismatch problems. Reducing mechanical mismatch provides a decreased risk of subsidence, stress shielding, bone resorption, and/or subsequent failure of adjacent peri-implant bone tissue. Additionally, scaffolds may include a significantly high porosity to promote bone ingrowth, while exhibiting significantly higher effective mechanical properties such as, for example, the mechanical properties of trabecular bone.

The example composite materials described herein may be used for applications such as, for example, synthetic bone graft substitutes, bone ingrowth surfaces applied to existing implants, tissue engineering scaffolds, interbody spinal fusion implants, osteotomy wedges, suture anchors, etc. In each of the applications, bone graft materials (e.g., autograft, demineralized bone matrix, and the like) may be incorporated into the central cavity (or "graft space") of the implant to further enhance osteoinduction and/or osteoconduction to promote osteointegration. Carrier materials (e.g., collagen, hydrogels, etc.) containing growth factors, such as bone morphogenetic proteins (BMP), may also be incorporated into the pore space of the scaffold and/or the central cavity (or "graft space") of the implant to further enhance osteoinduction and/or osteoconduction to promote osteointegration.

Suitable thermoplastic polymers that may be used herein include, but are not limited to, polyaryletherketone (PAEK), polyetheretherketone (PEEK), polyetherketonekteone (PEKK), polyetherketone (PEK), polyethylene, high density polyethylene (HDPE), ultra-high molecular weight polyethylene (UHMWPE), low density polyethylene (LDPE), polyethylene oxide (PEO), polyurethane, polypropylene, polypropylene oxide (PPO), polysulfone, polyethersulfone, polyphenylsulfone, poly(DL-lactide) (PDLA), poly(L-lactide) (PLLA), poly(glycolide) (PGA), poly($\epsilon$-caprolactone) (PCL), poly(dioxanone) (PDO), poly(glyconate), poly(hydroxybutyrate) (PHB), poly(hydroxyvalerate (PHV), poly (orthoesters), poly(carboxylates), poly(propylene fumarate), poly(phosphates), poly(carbonates), poly(anhydrides), poly (iminocarbonates), poly(phosphazenes), citric-acid based polymers, polyacrylics, polymethylmethacrylate (PMMA), bisphenol A-glycidyl methacrylate (bis-GMA), tri(ethylene glycol) dimethacrylate (TEG-DMA), copolymers thereof, and blends thereof.

Suitable bioactive reinforcement materials include, but are not limited to, hydroxyapatite (HA), calcium-deficient hydroxyapatite, carbonated calcium hydroxyapatite, beta-tricalcium phosphate (beta-TCP), alpha-tricalcium phosphate (alpha-TCP), amorphous calcium phosphate (ACP), anisometric calcium phosphate, octacalcium phosphate (OCP), tetracalcium phosphate, biphasic calcium phosphate (BCP), anhydrous dicalcium phosphate (DCPA), dicalcium phosphate dihydrate (DCPD), anhydrous monocalcium phosphate (MCPA), monocalcium phosphate monohydrate (MCPM), calcium silicates, calcium aluminates, calcium carbonate, calcium sulfate, zinc phosphate, zinc silicates, zeolites, silicon dioxide, silicon nitride, titanium, titanium dioxide, bioglass 45, bioglass 52S4.6, other glasses and glass-ceramics comprising $SiO_2$, CaO, $Na_2O$, $Al_2O_3$, and/or $P_2O_5$, and combinations thereof. Suitable bioactive reinforcement particles may also act antimicrobial materials which include, but are not limited to, silver, gold, selenium, copper, titanium dioxide, zinc oxide, cerium oxide, hafnium oxide, magnesium oxide, iron oxide, copper oxide. Other suitable reinforcement materials include, but are not limited to, carbon fibers, carbon nanotubes, graphene, fiberglass, polymer fibers, barium sulfate, zirconium oxide, aluminum oxide, other oxide particles, tantalum, nitinol, stainless steel, other metallic particles, and combinations thereof. An article formed according to the method, for example the biomedical implant (250) exemplified in FIG. 7-FIG. 9, may include any suitable combination of bioactive reinforcement materials and non-bioactive reinforcement materials.

Reinforcement materials, for example, reinforcements in the form of calcium phosphate reinforcement particles, may be in the form of single crystals or dense polycrystals and in some embodiments may be, at least in some portion, anisometric. As used herein, "anisometric" refers to any particle morphology (shape) that is not equiaxed (e.g., spherical), such as whiskers, plates, fibers, etc. Anisometric particles are usually characterized by an aspect ratio. For example, HA single crystals are characterized by the ratio of dimensions in the c- and a-axes of the hexagonal crystal structure. Thus, the anisometric particles in the present disclosure have an aspect ratio greater than 1. In one example, the mean aspect ratio of the reinforcement particles is from greater than 1 to about 100. In accordance with the various embodiments, the mean aspect ranges from greater than 1, to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, and up to and including about 100, including increments and ranges therein and there between.

The reinforcement particles, when present in a powder blend, can be provided in an amount of from about 1-99%, or from about 1-60% by volume of a powder blend, alternatively from about 20-50% by volume. In accordance with the various embodiments, the volume of reinforcement particles present in a powder blend can range from about 1-99%, or from about 1-60%, alternatively from about 5-50%, alternatively from about 10-40%, alternatively from about 15-25%, and any suitable combination, sub-combination, range, or sub-range thereof by volume, based on the volume of the powder blend. In particular, the amount of reinforcement particles present in a powder blend are represented as a percentage of the powder blend in the absence of and/or prior to addition of any porogen. Accordingly, while it is possible to express the amount of reinforcement in a blend that includes polymer, reinforcement and porogen, for purposes of the exemplified embodiments as described herein, the amount of reinforcement particles present in a powder blend are represented as a percentage of the powder blend of polymer(s) and inorganic particles (e.g., reinforcements) in the absence of and/or prior to addition of any porogen. Thus, the reinforcement particles may be present, by volume, based on the total volume of powder in a powder blend of polymer and reinforcement (i.e., prior to addition of any porogen), from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 84, 85, 86, 87, 88, 89, 90, 91, 92, 93, 94, 95, 96, 97, 98 to about 99 volume percent, including increments and ranges therein and there between.

Furthermore, there are no per se limits on the size of the inorganic particles (e.g., reinforcements). For example, the reinforcement particles may have a maximum dimension from about 5 nm to about 2 mm, and for example, between and including 20 nm to about 100 μm. While both nano- and micro-scale reinforcement particles improve the mechanical properties, nanoscale reinforcement particles are particularly effective for enhancing bioresorbability and cell attachment, and microscale particles are particularly effective for obtaining a uniform dispersion. Amongst suitable reinforcement particles, calcium phosphate particles are effective for increasing bioactivity. Thus, the reinforcement particles may have a size from about 5 nm to about 5, 10, 20, 30, 40, 50, 60, 70, 80, 90, 100, 200, 300, 400, 500, 600, 700, 800, 900 nm, and from about 1 μm to about 10, 20, 30, 40, 50, 60, 70, 80, 90, 100, 200, 300, 400, 500, 600, 700, 800, 900 μm, and to about 1 mm and up to and including about 2 mm, including increments and ranges therein and there between.

By way of example, a composite material may include a polyetheretherketone (PEEK) or a polyetherketoneketone (PEKK) matrix reinforced with various volume fractions of hydroxyapatite (HA) whiskers (e.g., 10, 20 or 40% by volume), wherein the thermoplastic polymer matrix may be approximately between and including 50% and 95% by volume porous and in some embodiments between and including 60% and 85% by volume porous, and in some particular embodiments between and including 65% and 75% by volume porous.

In some such embodiments, the thermoplastic polymer matrix may also include bone morphogenetic protein (BMP) such as, for example, rhBMP-2, which can be absorbed, dispersed, or accommodated by the void spaces and/or pores of the porous thermoplastic polymer scaffold or microporous polymer matrix. Additionally, the BMP may be adsorbed to the calcium phosphate reinforcements further localizing the BMP to the surface of the porous thermoplastic polymer scaffold.

The porous thermoplastic polymer scaffold may include a porous thermoplastic polymer (e.g., a PEEK polymer) scaffold having anisometric calcium phosphate reinforcement particles integrally formed or embedded with the porous thermoplastic scaffold and exposed on the surface of pores in the thermoplastic polymer scaffold. In this manner, the thermoplastic polymer matrix embedded with the reinforcement particles provides high material stiffness and strength, and the reinforcement particles exposed on the surface of the porous thermoplastic polymer scaffold promote bioactivity and/or bioresorption. The reinforcement particles may further provide radiopacity (contrast for radiographic imaging). The porous thermoplastic polymer scaffold includes a substantially continuous, interconnected porosity and a plurality of pores to promote bone ingrowth into the porous thermoplastic polymer scaffold. In addition, the porous thermoplastic polymer scaffold is substantially continuously interconnected via a plurality of struts. Furthermore, at least one of the plurality of struts may be a load-bearing strut.

Additionally, the thermoplastic polymer matrix may optionally include other additives, if suitable. By way of non-limiting example, the thermoplastic polymer matrix may include one or more surface-active agents to enhance interfacial bonding between the reinforcement particles and thermoplastic polymer. The void spaces and/or pores may accommodate and deliver one or more growth factors such as, for example, BMP-2, to enhance osteoinductivity and/or bone regeneration. Furthermore, the void spaces and/or pores may also accommodate and deliver one or more transcription factors, matrix metalloproteinases, peptides, proteins, bone cells, progenitor cells, blood plasma, bone marrow aspirate, or combinations thereof, to improve speed bone regeneration, or resorption and replacement of the biomaterial. In some examples, the void spaces and/or pores may further accommodate a carrier material that may be incorporated into the void spaces and/or pores. The carrier material may include, for example, a collagen sponge, membrane, or a hydrogel material to deliver the growth factor material such as, for example, the BMP-2. The calcium phosphate reinforcements exposed on the surface of the porous thermoplastic scaffold, along with the porosity, improve the retention and localization of the BMP-2 within the porous thermoplastic scaffold and at the peri-implant interface.

The porogen particles, when present in a powder blend, can be provided in an amount of from about 1-99%, including from 50% to about 90% by volume, and, for example, between and including about 70% to 90% by volume. In accordance with the various embodiments, the extent of porosity in a porous portion may range from 50% to about 95%, from about 55% to about 90%, from about 60% to about 85%, from about 65 to about 80% from about 65% to about 75%, from about 70% to about 75%, and any suitable combination, sub-combination, range, or sub-range thereof by volume, based on a volume porous portion and any suitable combination, sub-combination, range, or sub-range thereof by volume, based on the volume of the powder blend. Thus, the porogen particles may be present, by volume, based on the total volume of powder in a powder blend, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 49, 50, 51, 52, 53, 54, 55, 56, 57, 58, 59,60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 volume percent, including increments and ranges therein and there between.

Furthermore, the porogen particles may have a dimension or a size distribution in a range from about 0.1 μm to about 10 μm, including from about 0.1 μm to about 1 μm and from about 1 μm to about 10 μm, or from about 1 μm to about 100 μm, including from about 1 μm to about 10 μm and from about 10 μm to about 100 μm, or from about 10 μm to about 1,000 μm, including from about 10 μm to about 100 μm, from about 100 μm to about 1000 μm, from about 100 μm to about 500 μm, from about 200 μm to about 500 μm, from about 150 μm to about 450 μm, from about 200 μm to about 400 μm, from about 200 μm to about 300 μm, from about 250 μm to about 350 μm, from about 300 to about 350 μm, and any suitable combination, sub-combination, range, or sub-range thereof. Thus, the porogen particles may have a size or a size distribution in a range from about 0.1, 0.2, 0.3, 0.4, 0.5, 0.6, 0.7, 0.8, 0.8, 0.9, 1, 2, 3, 4, 5, 6, 7, 8, 9, 10, 20, 30, 40, 50, 60, 70, 80, 90, 100, 150, 200, 250, 300, 350, 400, 450, 500, 600, 700, 800, 900 to about 1000 μm (1 mm), including increments and ranges therein and there between.

In various embodiments, the porous regions may have pore sizes or a size distribution in a range between and including from about 10 μm to about 1,000 μm, and, for example, from about 300 μm to about 500 μm. In accordance with the various embodiments, porous regions may have pore sizes or a size distribution in a range from about 0.1 μm to about 10 μm, including from about 0.1 μm to about 1 μm and from about 1 μm to about 10 μm, or from about 1 μm to about 100 μm, including from about 1 μm to about 10 μm and from about 10 μm to about 100 μm, or from about 10 μm to about 1,000 μm, including from about 10 μm to about 100 μm, from about 100 μm to about 1000 μm, from about 100 μm to about 500 μm, from about 200 μm to about 500 μm, from about 150 μm to about 450 μm, from about 200 μm to about 400 μm, from about 200 μm to about 300 μm, from about 250 μm to about 350 μm, from about 300 to about 350 μm, and any suitable combination, sub-combination, range, or sub-range thereof. Accordingly, porous regions formed from a powder blend that includes at least one porogen material may include pores having sizes that are different, wherein at least a portion of the pores has a different size than other pores, each pore having a different size within the range from about from about 10 μm to about 1000 μm. Thus, porous regions may have pore sizes or a size distribution in a range from about 0.1, 0.2, 0.3, 0.4, 0.5, 0.6, 0.7, 0.8, 0.8, 0.9, 1, 2, 3, 4, 5, 6, 7, 8, 9, 10, 20, 30, 40, 50, 60, 70, 80, 90, 100, 150, 200, 250, 300, 350, 400, 450, 500, 600, 700, 800, 900 to about 1000 μm (1 mm), including increments and ranges therein and there between. It will be appreciated that pores in porous regions of the article assembly are formed upon the removal of porogen material included in a powder blend. It will further be appreciated that the particle size of any particular porogen may yield a pore that does not precisely match the size of the porogen particle either as a result of particle degradation or another artifact of the forming process, or differences or errors in measurement techniques.

In various embodiments, the porous regions may include an amount of porosity up to 99%, including from 50% to about 90% by volume, and, for example, between and including about 70% to 90% by volume. In accordance with the various embodiments, the extent of porosity in a porous portion may range from 50% to about 95%, from about 55% to about 90%, from about 60% to about 85%, from about 65% to about 80% from about 65% to about 75%, from about 70% to about 75%, and any suitable combination, sub-combination, range, or sub-range thereof by volume, based on a volume porous portion. Thus, the extent of pores, by volume, based on the total volume of a porous portion, can be from 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 to about 95 volume percent, including increments and ranges therein and there between.

In one embodiment, the thermoplastic composite body includes a ratio of cross-sectional area of at least one porous portion to at least one dense portion normal to loading that provides an overall stiffness for the thermoplastic composite body within 20% of adjacent vertebral bodies between which the implantable medical device is inserted. This ratio may be tailored with respect to the adjacent vertebral body composition, such as, by way of example, cancellous bone tissue or cortical bone tissue. In one embodiment, the at least one porous portion includes an elastic modulus within 20% of cancellous bone, and the at least one dense portion includes an elastic modulus within 20% of cortical bone. In one embodiment overall stiffness in axial (superior-inferior) compression is within 20% of that for adjacent cervical, thoracic and/or lumbar vertebral bodies which are known to exhibit a stiffness in axial compression in the range of about 0.5 to about 40 kN/mm, and more commonly from about 1 to about 6 kN/mm. The at least one dense portion may include an elastic modulus within 20% of that for cortical bone which is known to exbibit an elastic modulus in the range of about 5 to about 25 GPa. The at least one porous portion may include a compressive elastic modulus within 20% of that for cancellous bone, which is known to exhibit a compressive elastic modulus in the range of about 20 to about 1,000 MPa.

In some examples, the thermoplastic composite body includes a stiffness in axial (superior-inferior) compression less than about 20 kN/mm and a block stiffness in axial compression greater than at least about 800 N/mm. As used herein, "block stiffness" is a measure of how readily an implant subsides into adjacent bone superior and inferior to the implant upon loading in axial compression, as set forth in ASTM F2267. As known by one skilled in the art, a higher block stiffness indicates a greater resistance to subsidence, whereas a lower block stiffness indicates a lesser resistance to subsidence. According to some exemplified embodiments, the articles archive block stiffness that is greater than 1000 N/mm. In various embodiments according to the disclosure, articles formed by the inventive method may demonstrate block stiffness that is greater than 800 N/mm, or greater than 900 N/mm, or greater than 1000 N/mm, or greater than 1100 N/mm, or more.

The thermoplastic composite body may be non-destructively compressible in the direction of loading by at least about 10% of a thickness dimension, alternatively by at least about 15%, alternatively by at least about 20%, alternatively by at least about 25%, alternatively by at least about 30%, alternatively by at least about 35%, alternatively by at least about 40%, alternatively by at least about 45%, alternatively by at least about 50%. As used herein, "non-destructively compressible" indicates elastic or non-elastic compression without fracture of the thermoplastic composite body.

Referring to FIG. 1 in one embodiment, a method that may be used to prepare a thermoplastic composite body is provided. While an exemplary manner of synthesizing the thermoplastic composite body has been illustrated in FIG. 1 and FIG. 9, one or more of the steps and/or processes illustrated in FIG. 1 or FIG. 9 may be combined, divided, re-arranged, omitted, eliminated and/or implemented in any other way. Further still, the exemplary method of FIG. 1 may include one, or more processes and/or steps in addition to, or instead of, those illustrated in FIG. 1 or FIG. 9 and/or may include more than one of any or all of the illustrated processes and/or steps. Further, although the exemplary method is described with reference to the flow chart illustrated in FIG. 1, persons of ordinary skill in the art will readily appreciate that many other methods of synthesizing the example composite material may alternatively be used.

A thermoplastic composite body may be processed using a powder processing approach in conjunction with compression molding and particle leaching techniques and is particularly suited for achieving a relatively high concentration (e.g., >20% by volume) of well-dispersed anisometric calcium phosphate reinforcements (e.g., HA whiskers) in a thermoplastic matrix (e.g., PEEK) with minimal degradation of the calcium phosphate size/shape during processing. Compression molding the composite material may include aligning the reinforcement particles (e.g., HA whiskers) morphologically and/or crystallographically within the scaffold struts. In this manner, the calcium phosphate reinforcement volume fraction, aspect ratio, size and orientation; the polymer; and the size, volume fraction, shape and directionality of the void space and/or porosity may be tailored to vary the mechanical properties of the composite material.

A polymer such as, for example, PEEK, and reinforcements, such as HA whiskers, are provided in powder form. The PEEK polymer powder may have, for example, a mean particle size of about 10 µm, for example as described herein above. The HA whiskers may be synthesized using, for example, molten salt synthesis, hydrothermal synthesis, the chelate decomposition method, precipitation, solvothermal synthesis, precursor pyrolysis, solid state reactions, and the like.

In accordance with the various embodiments, polymer powders employed according to the disclosure can have a size that ranges from about 1 µm to about 500 µm or greater, including from about 1 µm to about 100 µm, from about 1 µm to about 75 µm, from about 1 to about 50 µm, from about 1 µm to about 25 µm, from about 1 µm to about 15 µm, from about 5 µm to about 10 µm, and any suitable combination, sub-combination, range, or sub-range thereof. The disclosure contemplates the use of one or more polymers, wherein each of the polymer powders may have a size that is the same or is different and may include a blend of polymers having the same or different sizes, wherein each polymer has a particle size in the range from about from about 1 µm to about 100 µm. Thus, the any one or more polymer powder may have a size from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400 and up to and including about µm, including increments and ranges therein and there between.

The polymer powder, for example, a PAEK polymer powder such as PEEK, and reinforcement, such as, for example, synthesized HA whiskers, optionally together with a porogen, as further described herein below, are co-dispersed, as a dry mixture. Of course, the powders could be blended in a suitable fluid that does not solvate any of the powders, and then dried prior to compression molding. And, of course, depending on the polymer selected, where for example the polymer is not a PAEK polymer, other forms of mixing may be employed for inclusion of a porogen, such as for example, solvent mixing.

In some embodiments, a combination of more than one powder for each component may be selected, for example, wherein each blend includes more than one or different polymers, more than one or different reinforcement powders, more than one or different porogens, or combinations of these. The amount of each component may be varied to obtain the desired mixture by the percentage of HA relative to the polymer powder and the percentage of HA and polymer powder relative to the porogen.

In one example, after the polymer powder and the reinforcement are mixed, the porosity of the composite material is selectively varied and/or tailored by any one of a variety of methods, for example as described below.

In one such example, the porosity may be formed and tailored by the addition of a suitable porogen material such as, for example, NaCl (sodium chloride), KCl (potassium chloride), wax, polysaccharides (sugars), cellulose, polymer or glass beads, and the like. Thus, in some embodiments, the porosity may be formed by a porogen that is selected from the group consisting of NaCl, KCl, wax, sugar, cellulose, polymer, glass beads, and combinations thereof. The extent of the porosity can be controlled by varying the amount of porogen used, and the pore size could be tailored by sieving the porogen to a desired size prior to mixing the porogen with the polymer mixture, or by selecting a porogen having a specified controlled size, or by blending one or more porogens of different sizes, or combinations of these. In various examples, one or more porogen employed for the formation of pores may have a size as described herein above.

In various examples, one or more porogen employed for the formation of pores may have any shape, which may be irregular or regular, for example, but not limited to, spheres, cubes, fibers, polyhedra, and the like. Indeed, a plurality of porogens may be used each having a different shape. In some particular examples, a porogen is select that has generally rounded surfaces.

The porous thermoplastic polymer scaffold or porous implant regions formed by compression molding undergoes a leaching process to remove the porogen. The leaching may occur, for example, via a dissolution method, heating method, and/or any other suitable methods and/or process(es). More specifically, dissolution may include immersing the molded article in a fluid, such as, for example, deionized water.

The shape of the unitary article, for example, a biomedical implant, may be formed by the mold walls and/or machining after molding. In some examples, the shapes of the parts may be achieved by computer numerical control (CNC) machining based on a computer-aided drawing (CAD)/computer-aided manufacturing (CAM) model according to methods that are generally known in the art.

The exemplified embodiments of implantable medical devices described herein are representative of implantable medical devices that include polymeric materials, for example, PAEK materials, that may include one or more of reinforcement particles and porosity. It will be appreciated that these materials may be used in accordance with the teachings herein for other bony implant applications, such as for implant fixation, fracture fixation, synthetic bone graft substitutes, interbody spinal fusion, osteotomy wedges, suture anchors, tissue engineering scaffolds, and other applications, and the implants may be tailored to provide specific mechanical, biological, and surgical functions by varying the distribution and proportions of dense and porous polymer, and by varying one or more of the polymer composition and molecular orientation, porosity and pore size of the porous thermoplastic scaffold, or the reinforcement, for example, HA, content, morphology, preferred orientation, and size.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated.

As used herein, the singular forms "a," "an," and "the" are intended to include the plural forms as well, unless the context clearly indicates otherwise. Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention.

All ranges and amounts given herein are intended to include subranges and amounts using any disclosed point as an end point. Similarly, a range given of "about 1 to 10 percent" is intended to have the term "about" modifying both the 1 and the 10 percent endpoints, and meaning within 10 percent of the indicated number (e.g. "about 10 percent" means 9-11 percent and "about 2 percent" means 1.8-2.2 percent). Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements. Thus, while exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

The above description is only illustrative of the preferred embodiments which achieve the objects, features and advantages of the present invention. It is not intended that the present invention be limited to the illustrated embodiments. While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

The invention claimed is:

1. A method for forming a unitary article, comprising the following steps:

i. provide at least two powder blends, each of the at least two powder blends being selected from the group consisting of at least one polymer powder, at least one polymer powder with at least one porogen powder, at least one polymer powder with at least one inorganic particle powder, and at least one polymer powder with at least one porogen powder and at least one inorganic particle powder, such that the at least two powder blends differ from one another in terms of content of the polymer powder, content of the porogen powder, content of the inorganic particle powder, or a combination thereof;

ii. dispense each of the at least two powder blends into at least one mold;

iii. compact each of the at least two powder blends into two or more parts with complementary mating surfaces;

iv. assemble the two or more parts with complementary mating surfaces to form an article assembly;

v. compression mold the article assembly to form a unitary article;

vi. optionally form additional features in the unitary article; and vii. leach porogen from the unitary article.

2. The method of claim 1, wherein the unitary article is a biomedical implant.

3. The method of claim 1, wherein the unitary article is free from discernible boundaries between portions of the unitary article derived from the two or more parts with complementary mating surfaces.

4. The method of claim 1, wherein the unitary article is free of metals other than bioactive reinforcement particles.

5. The method of claim 1, wherein step iii. includes compacting the at least two powder blends by cold pressing.

6. The method of claim 1, wherein the complementary mating surfaces of the two or more parts exhibit close tolerances for assembly.

7. The method of claim 1, wherein the at least one polymer powder of each of the at least two powder blends is the same.

8. The method of claim 1, wherein the at least one inorganic particle powder, when present in a powder blend of the at least two powder blends, is present in the range from about 1 to about 99 percent based on the total volume of the portion of the powder blend comprising the at least one polymer powder and the at least one inorganic particle powder, and wherein the at least one porogen powder, when present in a powder blend of the at least two powder blends, is present in the range from about 1 to about 99 percent based on the total volume of the powder blend comprising the at least one polymer powder and the at least one porogen powder.

9. The method of claim 1, wherein compression molding in one or more of the steps iii. and v. includes applying compression at a specified pressure to prevent volumetric expansion during heating.

10. The method of claim 1, wherein compression molding in one or more of the steps iii. and v. includes heating to the melting point of the at least one polymer powder and then cooling to a temperature just below the melting point of the at least one polymer powder, and applying pressure that is elevated over atmospheric to mold a preform of the two or more parts or the article assembly into a monolithic body, the step of applying pressure occurring at any point in time after heating above the melting temperature of the at least one polymer powder and up to and through cooling to a temperature below the melting temperature but above the glass transition temperature of the at least one polymer powder.

11. The method of claim 1, further including modifying a surface of the unitary article with a surface modification process altering at least one of surface composition, surface roughness, or surface porosity.

12. The method of claim 11, wherein the surface modification process is selected from the group consisting of:

a thermal spray process;
media blasting;
plasma treatment;
pressing a sacrificial porogen into the surface;
a vapor-based surface modification process;
a chemical solution deposition process;
and combinations thereof.

13. The method of claim 11, wherein the surface modification process forms a superficial coating of hydroxyapatite on a surface of the unitary article.

14. The method of claim 11, wherein step iii. further includes machining at least one of the two or more parts to form the complementary mating surfaces.

15. A method for forming a unitary article, comprising the following steps:

i. assembling two or more parts with complementary mating surfaces to form an article assembly, at least one of the two or more parts with complementary mating surfaces including at least one porogen;

ii. compression molding the article assembly to form a unitary article free from discernible boundaries between portions of the unitary article derived from the two or more parts with complementary mating surfaces;

iii. optionally forming additional features in the unitary article; and iv. leaching the at least one porogen from the unitary article, wherein at least one of the two or more parts with complementary mating surfaces is formed by:

dispensing a powder blend into at least one mold, the powder blend including:

at least one polymer powder;

the at least one porogen in powder form; and optionally, at least one inorganic particle powder;

compacting the powder blend in the at least one mold to form at least one preform.

16. The method according to claim 15, wherein the unitary article is a biomedical implant.

17. The method according to claim 15, wherein the unitary article is free of metals other than bioactive reinforcement particles.

18. A method for forming a unitary article, comprising the following steps:

i. assembling two or more parts with complementary mating surfaces to form an article assembly, at least one of the two or more parts with complementary mating surfaces including at least one porogen;

ii. compression molding the article assembly to form a unitary article free from discernible boundaries between portions of the unitary article derived from the two or more parts with complementary mating surfaces;

iii. optionally forming additional features in the unitary article; and iv. leaching the at least one porogen from the unitary article.

19. The method according to claim 18, wherein the unitary article is a biomedical implant.

20. The method according to claim 18, wherein the unitary article is free of metals other than bioactive reinforcement particles.

* * * * *